United States Patent
Silawan et al.

(10) Patent No.: US 10,863,939 B2
(45) Date of Patent: Dec. 15, 2020

(54) EMOTION ESTIMATING METHOD, EMOTION ESTIMATING APPARATUS, AND RECORDING MEDIUM STORING PROGRAM

(71) Applicant: Panasonic Intellectual Property Corporation of America, Torrance, CA (US)

(72) Inventors: Nawatt Silawan, Osaka (JP); Koichi Kusukame, Nara (JP); Shinji Uchida, Osaka (JP); Shinichi Shikii, Nara (JP); Aki Yoneda, Hyogo (JP); Tatsuo Itoh, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 263 days.

(21) Appl. No.: 15/288,866

(22) Filed: Oct. 7, 2016

(65) Prior Publication Data

US 2017/0105662 A1  Apr. 20, 2017

Related U.S. Application Data

(60) Provisional application No. 62/241,374, filed on Oct. 14, 2015.

(30) Foreign Application Priority Data

Feb. 18, 2016  (JP) .................................. 2016-029363

(51) Int. Cl.
  *A61B 5/16*   (2006.01)
  *G06K 9/00*   (2006.01)
  (Continued)

(52) U.S. Cl.
  CPC ............ *A61B 5/165* (2013.01); *A61B 5/0077* (2013.01); *A61B 5/021* (2013.01); *A61B 5/026* (2013.01);
  (Continued)

(58) Field of Classification Search
  CPC ........... G06K 9/00302; G06K 9/00308; G06K 9/00315; G06K 2009/00322;
  (Continued)

(56) References Cited

U.S. PATENT DOCUMENTS

2003/0009078 A1* 1/2003 Fedorovskaya .... A61B 5/02055
                                                          600/26
2005/0283055 A1  12/2005 Shirai et al.
(Continued)

FOREIGN PATENT DOCUMENTS

CN   102933136 A   2/2013
JP   2006-006355 A   1/2006
(Continued)

OTHER PUBLICATIONS

The Extended European Search Report dated Mar. 2, 2017 for European Patent Application No. 16193718.0.
(Continued)

*Primary Examiner* — Christopher A Flory
*Assistant Examiner* — Nathan A Baldwin
(74) *Attorney, Agent, or Firm* — Greenblum & Bernstein. P.L.C.

(57) ABSTRACT

An emotion estimating method includes: acquiring first data and second data from the subject, the first data corresponding to physiology data, and the second data corresponding to one of physiology data different from the first data and non-physiology data; calculating a first value and a second value based on the acquired first data and second data, the first value indicating a degree of arousal of the subject and
(Continued)

the second value indicating a degree of valence of the subject; estimating the emotion of the subject, by using the calculated first value and second value and based on a predetermined association of people's emotions with a degree of arousal and a degree of valence of the people, the predetermined association being pre-stored in a memory; and outputting information indicating the estimated emotion.

16 Claims, 24 Drawing Sheets

(51) Int. Cl.
| | |
|---|---|
| *H04N 21/442* | (2011.01) |
| *A61B 5/00* | (2006.01) |
| *A61B 5/1171* | (2016.01) |
| *A61B 5/0205* | (2006.01) |
| *A61B 5/021* | (2006.01) |
| *A61B 5/026* | (2006.01) |
| *A61B 5/0476* | (2006.01) |
| *A61B 5/053* | (2006.01) |
| *A61B 5/08* | (2006.01) |
| *A61B 5/11* | (2006.01) |
| *A61B 5/145* | (2006.01) |
| *G06K 9/62* | (2006.01) |
| *G10L 25/63* | (2013.01) |

(52) U.S. Cl.
CPC ...... *A61B 5/02055* (2013.01); *A61B 5/02108* (2013.01); *A61B 5/0476* (2013.01); *A61B 5/053* (2013.01); *A61B 5/0816* (2013.01); *A61B 5/11* (2013.01); *A61B 5/1171* (2016.02); *A61B 5/14542* (2013.01); *A61B 5/4803* (2013.01); *A61B 5/7264* (2013.01); *G06K 9/00302* (2013.01); *H04N 21/44218* (2013.01); *A61B 5/1128* (2013.01); *G06F 2203/011* (2013.01); *G06K 9/6289* (2013.01); *G06K 2009/00939* (2013.01); *G06K 2209/27* (2013.01); *G10L 25/63* (2013.01)

(58) Field of Classification Search
CPC ............ G06K 2009/00328; A61B 5/16; A61B 5/165; A61B 5/167; A61B 5/168
See application file for complete search history.

(56) References Cited

U.S. PATENT DOCUMENTS

| | | | |
|---|---|---|---|
| 2006/0004266 A1* | 1/2006 | Shirai | A61B 5/165 600/300 |
| 2009/0285456 A1* | 11/2009 | Moon | G06K 9/00335 382/118 |
| 2011/0077996 A1* | 3/2011 | Ahn | A61B 5/053 705/7.29 |
| 2011/0105857 A1* | 5/2011 | Zhang | G11B 27/034 600/300 |
| 2011/0300847 A1* | 12/2011 | Quy | H04W 4/00 455/419 |
| 2011/0301433 A1 | 12/2011 | Sadowsky et al. | |
| 2013/0018837 A1* | 1/2013 | Lee | A61B 5/165 706/52 |
| 2014/0223462 A1* | 8/2014 | Aimone | A61B 5/0476 725/10 |
| 2014/0253709 A1* | 9/2014 | Bresch | H04N 7/18 348/77 |
| 2015/0173631 A1* | 6/2015 | Richards | A61B 5/02427 600/479 |
| 2016/0042648 A1* | 2/2016 | Kothuri | G06F 3/015 434/236 |
| 2016/0259977 A1* | 9/2016 | Asbun | A61B 5/165 |
| 2016/0360970 A1* | 12/2016 | Tzvieli | A61B 5/015 |
| 2017/0071551 A1* | 3/2017 | Jain | A61B 5/0006 |

FOREIGN PATENT DOCUMENTS

| | | |
|---|---|---|
| JP | 2007-128227 A | 5/2007 |
| JP | 2012-059107 A | 3/2012 |
| JP | 2013-027570 A | 2/2013 |
| JP | 2013-099373 | 5/2013 |
| JP | 2013-537435 A | 10/2013 |

OTHER PUBLICATIONS

English Translation of Chinese Search Report from The Patent Office of the People's Republic of China dated May 22, 2020 for the related Chinese Patent Application No. 201610877349.2.

* cited by examiner

FIG. 27

Registration of Subject Information

Nationality: ⊘  Blood Pressure: Minimum: 60  Maximum: 120

Gender: ♂  Skin Color: ▨

Age: 33  Chronic Disease: ⋯

Average Heart Rate: 70

FIG. 28

Registration of Face of Subject

281 — [face image]

Average Heart Rate: 70 — 282

Average Respiration Rate: 0.88 — 283

For face registration, please make a normal facial expression.

Enter — 284

FIG. 32
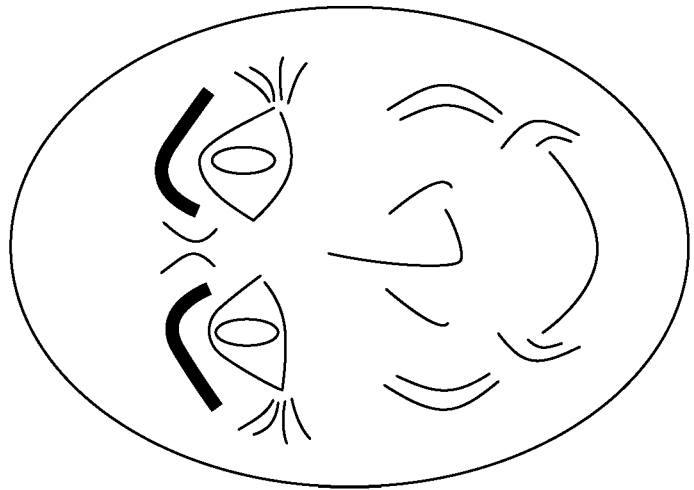
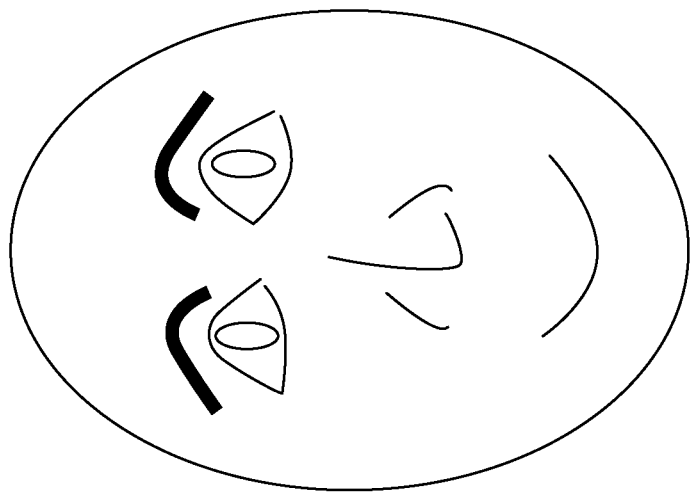

EMOTION ESTIMATING METHOD, EMOTION ESTIMATING APPARATUS, AND RECORDING MEDIUM STORING PROGRAM

BACKGROUND

1. Technical Field

The present disclosure relates to an emotion estimating method, an emotion estimating apparatus, and a recording medium storing a program.

2. Description of the Related Art

Japanese Patent No. 5768667 discloses an analyzing apparatus that evaluates, based on a person's facial expression or the like acquired by a sensor, information indicating a possibility that the facial expression or the like is a natural expression of the emotion of the person.

SUMMARY

In one general aspect, the techniques disclosed here feature an emotion estimating method for an emotion estimating apparatus for estimating an emotion of a subject. The emotion estimating method includes: acquiring first data and second data from the subject, the first data corresponding to physiology data, and the second data corresponding to one of physiology data different from the first data and non-physiology data; calculating a first value and a second value based on the acquired first data and second data, the first value indicating a degree of arousal of the subject and the second value indicating a degree of valence of the subject; estimating the emotion of the subject, by using the calculated first value and second value and based on a predetermined association of people's emotions with a degree of arousal and a degree of valence of the people, the predetermined association being pre-stored in a memory; and outputting information indicating the estimated emotion.

In the emotion estimating method in the present disclosure, it is possible to estimate various emotions felt by a person.

It should be noted that general or specific embodiments may be implemented as a system, a method, an integrated circuit, a computer program, a computer-readable storage medium such as a compact disc read-only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 27 is a schematic view of an image for registering subject information according to the embodiment;

FIG. 28 is a schematic view of a first example of an image for registering the face of the subject according to the embodiment;

FIG. 32 illustrates an example of a screen for prompting the user to select whether or not information regarding wrinkles of the face is to be used when the emotion estimating apparatus makes a facial-expression or emotion determination.

DETAILED DESCRIPTION (Knowledge Underlying Present Disclosure)

Figure 1:
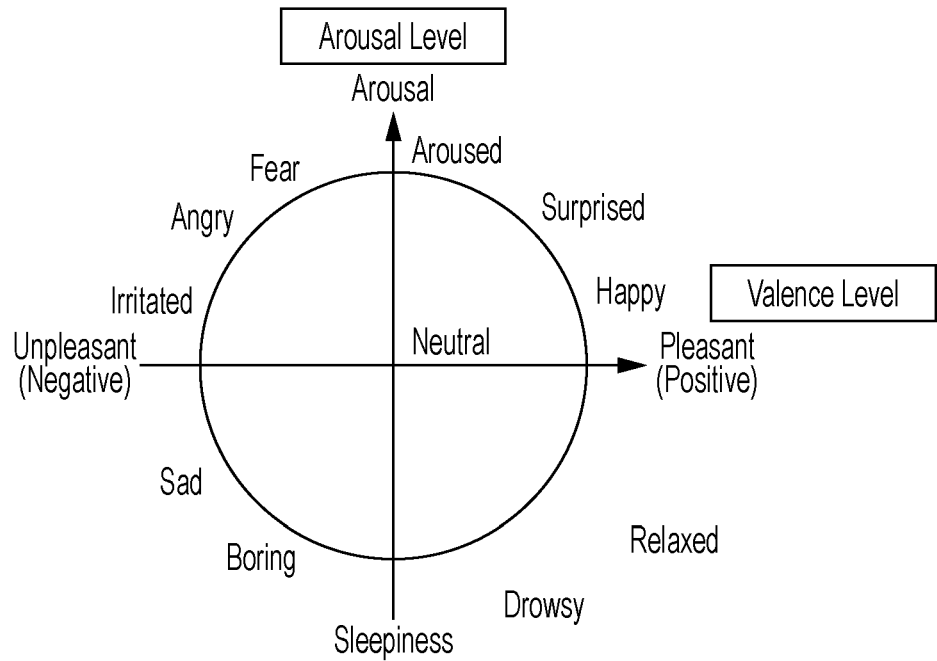
FIG. 1 is a diagram illustrating one example of a two-dimensional model of human emotions.

The technology disclosed in Japanese Patent No. 5768667 has a problem in that various emotions, such as happiness and surprise, felt by people cannot be evaluated.

Accordingly, the present disclosure provides an emotion estimating apparatus and so on that estimate various emotions felt by people.

An emotion estimating method according to one aspect of the present disclosure is directed to an emotion estimating method for an emotion estimating apparatus for estimating an emotion of a subject. The emotion estimating method includes: acquiring first data and second data from the subject, the first data corresponding to physiology data, and the second data corresponding to one of physiology data different from the first data and non-physiology data; calculating a first value and a second value based on the acquired first data and second data, the first value indicating a degree of arousal of the subject and the second value indicating a degree of valence of the subject; estimating the emotion of the subject, by using the calculated first value and second value and based on a predetermined association of people's emotions with a degree of arousal and a degree of valence of the people, the predetermined association being pre-stored in a memory; and outputting information indicating the estimated emotion.

According to the above-described aspect, the emotion estimating apparatus in an embodiment can estimate an emotion of a subject on the basis of the predetermined association and through use of two or more pieces of data including physiology data acquired from the subject and physiology data different from that physiology data or non-physiology data acquired from the subject. Through use of the two or more pieces of data, the emotion estimating apparatus disclosed herein calculates two indicators, that is, a first value (an arousal level) and a second value (a valence level) of a subject, thereby making it possible to appropriately estimate various emotions felt by the subject.

For example, the second data may be non-physiology data.

According to the above-described aspect, through use of the physiology data and non-physiology data acquired from the subject and based on the predetermined association, the emotion estimating apparatus can estimate an emotion of the subject. The physiology data has a relatively high correlation with the arousal level, and the non-physiology data has a relatively high correlation with the valence level. Hence, when the physiology data and the non-physiology data are used, the arousal level and the valence level can be more accurately calculated, and thus, the emotion of the subject can be estimated with higher accuracy.

For example, in the calculating, the first value may be calculated based on the first data, and the second value may be calculated based on the second data.

According to the above-described aspect, the emotion estimating apparatus calculates an arousal level having a relatively high correlation with the physiology data through use of the physiology data acquired from the subject, and calculates a valence level having a relatively high correlation with the non-physiology data through use of the non-physiology data. Hence, the arousal level and the valence level can be more accurately calculated, and thus, the emotion of the subject can be estimated with higher accuracy.

For example, the emotion estimating apparatus may comprise a camera that captures an image of the subject's face to generate moving-image data; and in the acquiring, a heart rate of the subject may be acquired as the first data, based on the moving-image data generated by the camera, and a facial expression of the subject may be acquired as the second data, the facial expression being identified based on a position of a feature point on the subject's face in the moving-image data generated by the camera.

According to the above-described aspect, the emotion estimating apparatus obtains both the heart rate, which is physiology data, of the subject and a facial expression, which is non-physiology data, by using a camera and estimates the emotion of the subject. Thus, when both the physiology data and the non-physiology data are obtained using one device, which is a camera, to estimate the emotion, the amount of burden on the subject is reduced, and convenience improves.

For example, in the outputting, a point in a plane with two coordinate axes indicating the first value and the second value may be output on a display screen of a display device as information indicating the emotion of the subject, the display device being included in the emotion estimating apparatus.

According to the above-described aspect, the emotion estimating apparatus outputs the arousal level and the valence level of the subject by representing the arousal level and the valence level as a point in a plane. This allows the user or the subject to intuitively know which of various possible subject emotions the emotion of the subject corresponds and also the intensity of the emotion of the subject.

For example, in the outputting, at least one of the first value and the second value may be output on a display screen of a display device as information indicating the emotion of the subject, the display device being included in the emotion estimating apparatus.

According to the above-described aspect, the emotion estimating apparatus outputs at least one of the arousal level and the valence level of the subject. As a result of the outputting, the user or the subject can know not only the emotion of the subject but also the arousal level and/or the valence level felt by the subject.

For example, in the outputting, a value indicating an intensity of a predetermined emotion of the subject may be output on a display screen of a display device as information indicating the emotion of the subject, the display device being included in the emotion estimating apparatus.

According to the above-described aspect, the emotion estimating apparatus outputs the intensity of a particular emotion (e.g., happiness) of the subject (in other words, the degree of an emotion). For example, the emotion estimating apparatus outputs not only an emotion "happiness" but also the degree of happiness. This allows the user or the subject to know not only the emotion of the subject but also the intensity or degree of the emotion.

For example, in the calculating, a first reliability that is an indicator indicating correctness of an emotion of the subject, the emotion being estimated based on the first value, may be calculated, and a second reliability that is an indicator indicating correctness of an emotion of the subject, the emotion being estimated based on the second value, may be calculated; and in the outputting, information indicating at least one of the first reliability and the second reliability may be output together with the information indicating the estimated emotion.

According to the above-described aspect, the emotion estimating apparatus outputs, as reliabilities, the level of correctness at which the estimated emotion represents the emotion of the subject. This allows the user or the subject to know not only the emotion of the subject but also the level of correctness at which the emotion represents the emotion of the subject.

For example, the first data acquired in the acquiring may include one or more pieces of first data, and the second data acquired in the acquiring may include one or more pieces of second data; and in the calculating, a first value and a first reliability may be calculated for each of the acquired one or more pieces of first data, the first value may be a value resulting from weighted average using the first reliability for the first value as a weight, a second value and a second reliability may be calculated for each of the acquired one or more pieces of second data, and the second value may be a value resulting from weighted average using the second reliability for the second value as a weight.

According to the above-described aspect, when the arousal level or the valence level can be obtained from a plurality of pieces of physiology data and non-physiology data, the emotion estimating apparatus can estimate an emotion of the subject by appropriately evaluating the plurality of pieces of physiology data and non-physiology data on the basis of the reliabilities.

For example, in the outputting, when at least one of the first reliability and the second reliability is smaller than a predetermined threshold, a warning may be output.

According to the above-described aspect, the emotion estimating apparatus outputs a warning when the estimated emotion does not so correctly represent the emotion of the subject. This allows the user or the subject to clearly know that the estimated emotion does not so correctly represent the emotion of the subject.

For example, in the calculating, the first data may be compared with a predetermined first reference value to calculate the first value, and the second data may be compared with a predetermined second reference value to calculate the second value; and the emotion estimating method may further include: obtaining information relevant to a physical characteristic of the subject; and adjusting the predetermined first reference value or the predetermined second reference value, based on the obtained information relevant to the physical characteristic of the subject.

According to the above-described aspect, by varying the reference values for the arousal level and the valence level on the basis of information (e.g., the gender or age) relevant to a physical characteristic of the subject, the emotion estimating apparatus can adjust the arousal level and the valence level in accordance with the physical characteristic of the subject and can more appropriately estimate the emotion.

For example, the emotion estimating method may further include receiving, from a user, a selection of an area included in a plurality of predetermined areas of a human face and used for acquiring a facial expression that is the second data. In the acquiring, a feature point included in the area of the subject's face may be acquired as the second data; and in the calculating, the second value may be calculated based on the feature point included in the area of the subject's face.

According to the above-described aspect, upon receiving a setting for the face area for acquiring a facial expression of the subject, the emotion estimating apparatus acquires a facial expression of the subject by using the received setting. For example, when the subject wears sunglasses, the portion of the eyes of the subject is hidden by the sunglasses, and thus information regarding a facial expression cannot be obtained from the eye portion. In such a case, the emotion estimating apparatus is adapted to obtain a facial expression of the subject from a portion other than the eye portion of the subject to thereby make it possible to more appropriately detect the facial expression.

For example, the physiology data may include at least one of face color, a heart rate, a heart rate variation, the low frequency/high frequency (LF/HF) of a heart rate variation, an R wave to R wave (R-R) interval, a pulse wave, a pulse variation, a brain wave, a respiration rate, a respiratory volume, a blood flow, a blood flow variation, a blood pressure, a blood pressure variation, an oxygen saturation level, movement of a part of a human body, movement of a muscle of a human body, movement of a muscle of a face, a body temperature, a skin temperature, a skin conductance, a skin resistance, an amount of sweat, and a perspiration rate.

According to the above-described aspect, by using the physiology data, such as facial color, the emotion estimating apparatus can more specifically estimate an emotion felt by the subject.

For example, the non-physiology data may include at least one of a facial expression, an emotion, a touch input signal, voice, a linguistic representation, a sentence, and body motion.

According to the above-described aspect, by using the non-physiology data, such as a facial expression, the emotion estimating apparatus can more specifically estimate an emotion felt by the subject.

For example, the predetermined first reference value or the predetermined second reference value may be calculated based on at least one of a gender, nationality, age, and skin color of the subject.

According to the above-described aspect, by using the information, such as gender, the emotion estimating apparatus can more specifically estimate an emotion felt by the subject.

Also, a processor may perform at least one of the acquiring, the calculating, the estimating, and the outputting.

An emotion estimating apparatus according to one aspect of the present disclosure is directed to an emotion estimating apparatus including: an acquirer that acquires first data and second data from a subject, the first data corresponding to physiology data, and the second data corresponding to one of physiology data and non-physiology data and being different from the first data; an estimator (i) that calculates a first value and a second value based on the acquired first data and second data, the first value indicating a degree of arousal of the subject and the second value indicating a degree of valence of the subject, and (ii) estimates the emotion of the subject, by using the calculated first value and second value and based on a predetermined association of people's emotions with a degree of arousal and a degree of valence of the people, the predetermined association being pre-stored in a memory; and an outputter that outputs information indicating the estimated emotion.

At least one of the acquirer, the estimator, and the outputter may include a processor.

The above-described aspect offers advantages that are analogous to those of the above-described emotion estimating apparatus.

Also, a recording medium according to one aspect of the present disclosure is directed to a non-transitory recording medium storing a computer program. The program causes a computer to execute: acquiring first data and second data from a subject, the first data corresponding to physiology data, and the second data corresponding to one of physiology data and non-physiology data and being different from the first data; calculating a first value and a second value based on the acquired first data and second data, the first value indicating a degree of arousal of the subject and the second value indicating a degree of valence of the subject; estimating the emotion of the subject, by using the calculated first value and second value and based on a predetermined association of people's emotions with a degree of arousal and a degree of valence of the people, the predetermined association being pre-stored in a memory; and outputting information indicating the estimated emotion.

The above-described aspect offers advantages that are analogous to those of the above-described emotion estimating apparatus.

It should be noted that general or specific embodiments may be implemented as a system, a method, an integrated circuit, a computer program, a computer-readable storage medium such as a CD-ROM, or any selective combination thereof.

Embodiments will be described below in detail with reference to the accompanying drawings.

The embodiments described below each represent a general or specific example. Numerical values, shapes, materials, constituent elements, the arrangement and connection of constituent elements, steps, the order of steps, and so on described in the embodiments below are examples, and are not intended to limit the present disclosure. Of the constituent elements in the embodiments described below, the constituent elements not set forth in the independent claims that represent the broadest concept will be described as optional constituent elements.

Embodiments

In the present embodiment, a description will be given of an emotion estimating apparatus for estimating various emotions felt by a person and an emotion estimating method for the emotion estimating apparatus. In the following description, a person whose emotion is to be estimated by an emotion estimating apparatus is referred to as a "subject", and a person who operates the emotion estimating apparatus is referred to as a "user". The subject and the user may be the same person.

FIG. 1 is a diagram illustrating one example of a two-dimensional model of human emotions. More specifically, the two-dimensional emotion model illustrated in FIG. 1 is called Russell's circumplex model.

People feel various emotions, including happiness and surprise. In FIG. 1, various emotions felt by people are arranged in a plane with two axes indicating an arousal level representing a degree of arousal and a valence level representing a degree of valence. It has been known that, as illustrated in FIG. 1, various emotions felt by people can be arranged in a circular ring in the plane.

The present inventors have obtained a result indicating that an estimation result and an actual emotion do not match well when emotion estimation based on Russell's circumplex model is performed using only a facial expression of a subject. As a result of a great deal of consideration in this respect, the present inventors have found that non-physiology data, particularly a facial expression, has a high correlation with the valence level in Russell's circumplex model and has a small correlation with the arousal level. The inventors also have found that the arousal level in Russell's circumplex model has a high correlation with physiology data, such as a heart rate.

On the basis of the above-described findings, the inventors made this disclosure by paying attention to the idea that emotion estimation using Russell's circumplex model can be performed with higher accuracy through appropriate use of non-physiology data and physiology data.

The emotion estimating apparatus according to the present embodiment estimates various emotions felt by a subject, by using physiology data or non-physiology data and based on the above-described correlation. The configuration and the operation of the emotion estimating apparatus will be described below in order.

Figure 2:
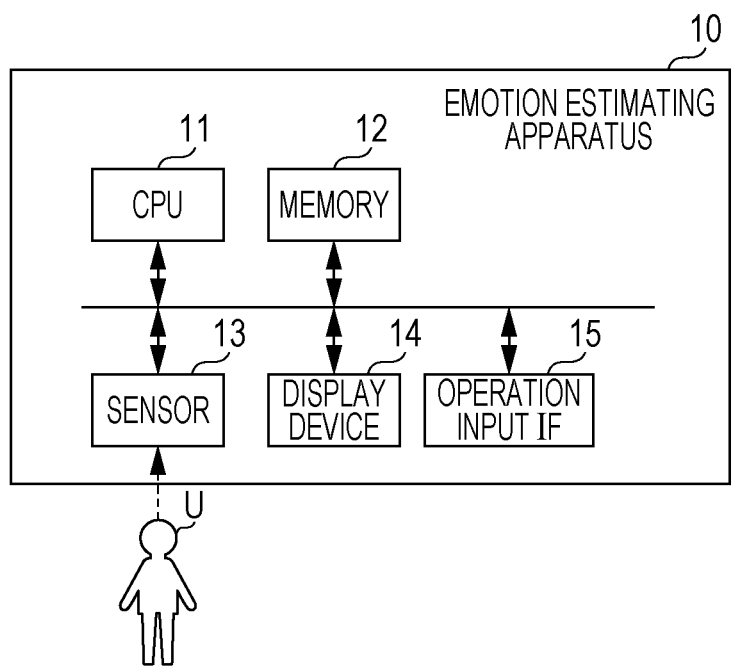
FIG. 2 is a block diagram illustrating the hardware configuration of an emotion estimating apparatus according to an embodiment.

FIG. 2 is a block diagram illustrating the hardware configuration of an emotion estimating apparatus 10 according to the present embodiment.

As illustrated in FIG. 2, the emotion estimating apparatus 10 includes a central processing unit (CPU) 11, a memory 12, a sensor 13, a display device 14, and an operation input interface (IF) 15.

The CPU 11 is a processor for executing a control program stored in the memory 12. The CPU 11 executes the control program to thereby realize each functional block (described below) in the emotion estimating apparatus 10.

The memory 12 is a storage device and includes a volatile storage area used as work area when the CPU 11 executes the control program and a nonvolatile storage area in which the control program and so on are held.

The sensor 13 is a sensor for acquiring physiology data or non-physiology data of a human subject U from the subject U. The sensor 13 includes a plurality of sensor elements. Each of the sensor elements acquires the physiology data or non-physiology data by detecting the physiology data or non-physiology data from the subject U. At least one of the sensor elements is a sensor element (a physiology sensor) for acquiring physiology data. Each sensor element other than the at least one sensor element may be a physiology sensor or may be a sensor element (a non-physiology sensor) for acquiring non-physiology data.

The physiology data is data related to a biological function and includes at least one of, for example, face color, a heart rate, a heart rate variation, the low frequency/high frequency (LF/HF) of a heart rate variation, an R wave to R wave (R-R) interval, a pulse wave, a pulse variation, a brain wave, a respiration rate, a respiratory volume, a blood flow, a blood flow variation, a blood pressure, a blood pressure variation, an oxygen saturation level (SO2), movement of a part of a human body, movement of a muscle of a human body, movement of a muscle of a face, a body temperature, a skin temperature, a skin conductance, a skin resistance, a skin roughness, a skin shininess, an amount of sweat, and a perspiration rate. Examples of the movement of the parts of the human body include the frequency of blinking, and the speed of blinking. The physiology data is also referred to as "non-face-expression data", in contrast to "facial expression data".

The physiology sensor includes at least one of, for example, a camera (a visible light camera or a camera having a particular electromagnetic wave filter), an electrocardiogram sensor (EKG or ECG), a photoplethysmographic sensor, an electroencephalogram device (EEG), a spirometer, a respiratory activity measuring instrument, a time-of-flight (TOF) sensor, a millimeter-wave sensor, a millimeter-wave radar, a pulse oximeter, a thermographer, a thermal imager, an infrared imager, a detector for face muscle movement, a skin temperature conductance sensor, a skin resistance sensor, an amount-of-sweat sensor, a near-infrared spectrometer, and a computed tomography (CT) apparatus.

The non-physiology data is data that is related to a biological body and that is not physiology data. The non-physiology data includes at least one, of, for example, a facial expression, an emotion, a touch input signal, voice, a linguistic representation, a sentence, and body motion (a gesture). An emotion acquired as non-physiology data is not an emotion estimated by the emotion estimating apparatus 10 and is an emotion acquired from another method, and, for example, is input by the subject U as his or her emotion. Of the non-physiology data, for example, data used for estimating a facial expression, such as information (the position and/or the shape of the mouth, an eye, or an eyebrow) that can be read from an image of the face, is referred to as "facial expression data".

The non-physiology sensor includes, for example, at least one of a camera, an emotion detecting device, a touch input unit (a touch screen), a microphone, a TOF sensor, a millimeter-wave sensor, a millimeter-wave radar, a keyboard for inputting a word or sentence, and a gait sensor.

The display device 14 is one example of a device for outputting various types of information and has a display screen for displaying various types of information as images. The display device 14 is, for example, a display portion of a touch panel display.

The operation input IF 15 receives a user's operation on the emotion estimating apparatus 10. The operation input IF 15 is, for example, a touch panel portion of a touch panel display.

Figure 3:
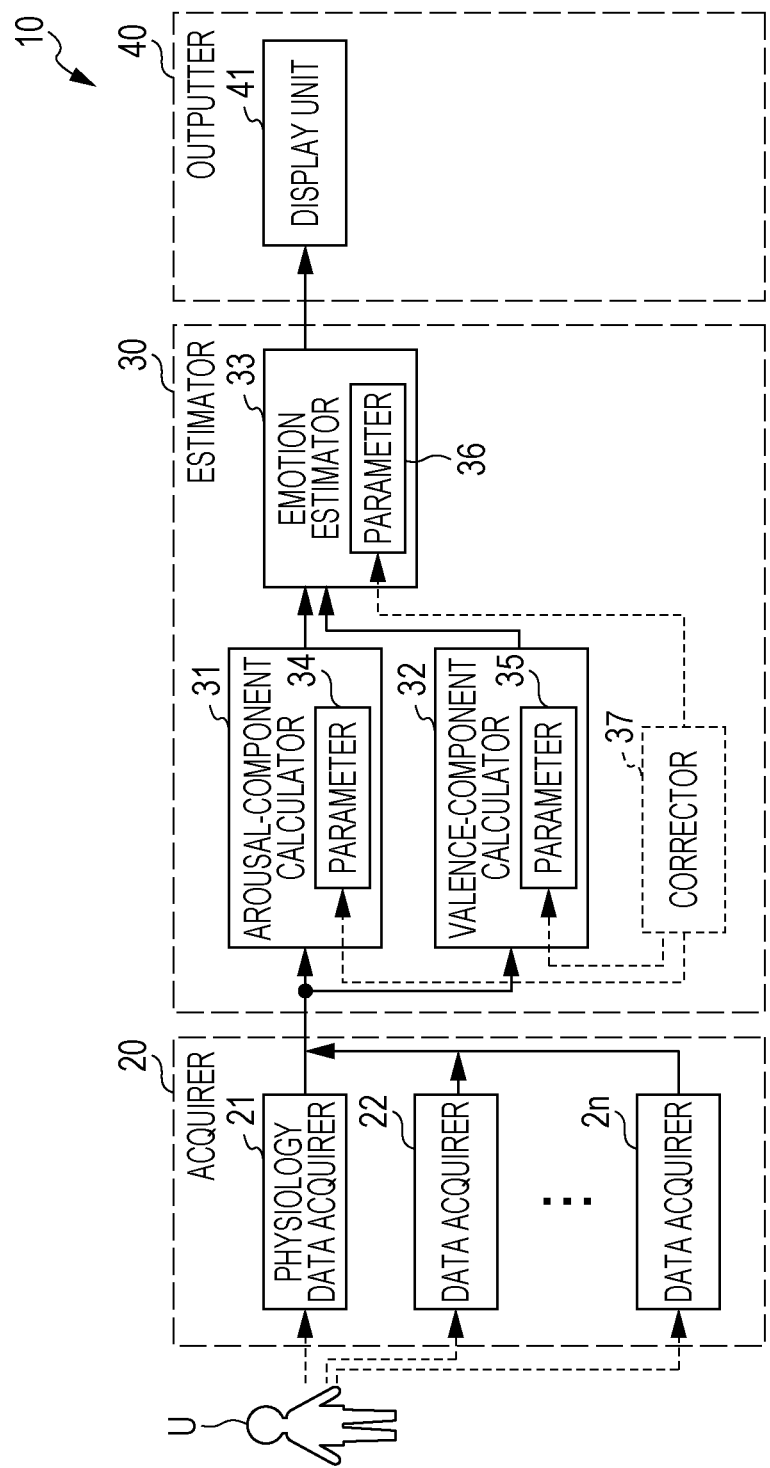
FIG. 3 is a block diagram illustrating the functional configuration of the emotion estimating apparatus according to the embodiment.
Figure 4:
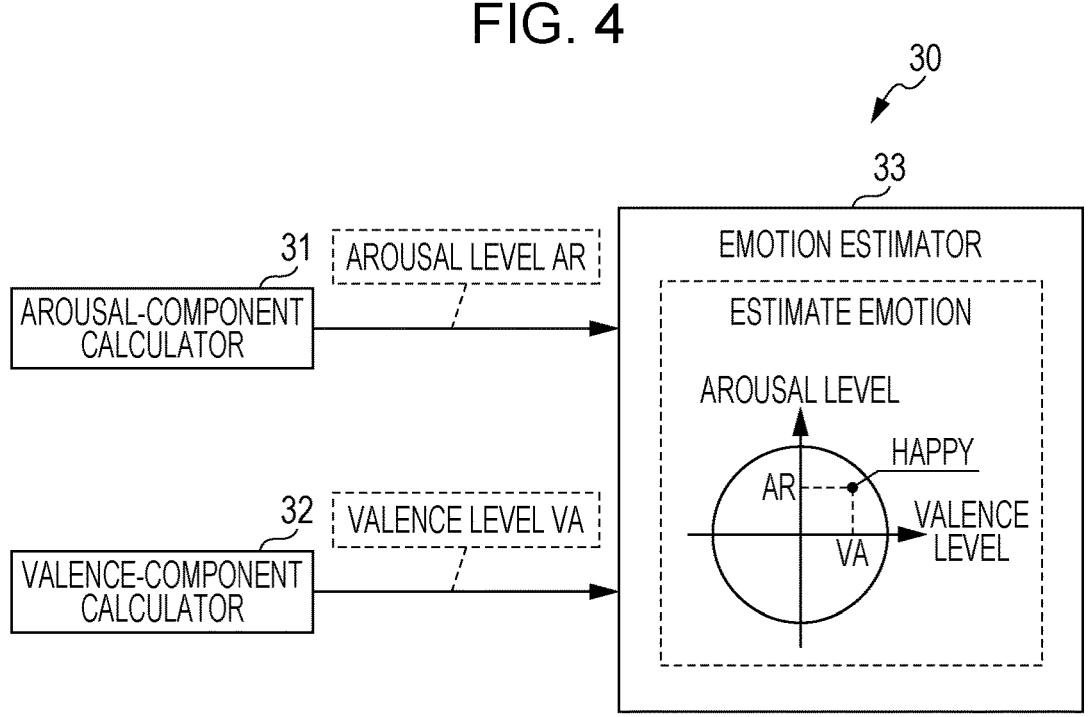
FIG. 4 is a schematic diagram illustrating an emotion estimating method executed by the emotion estimating apparatus according to the embodiment.
Figure 5:
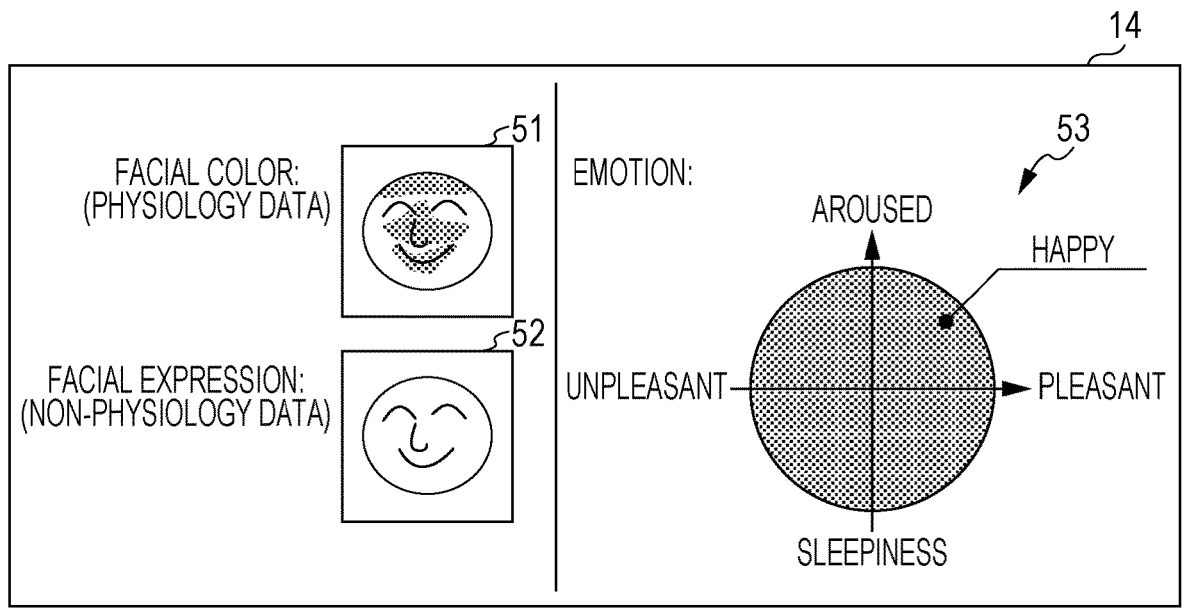
FIG. 5 is a schematic diagram illustrating an emotion output method executed by the emotion estimating apparatus according to the embodiment.

FIG. 3 is a block diagram illustrating the functional configuration of the emotion estimating apparatus 10 according to the present embodiment. FIG. 4 is a schematic diagram illustrating an emotion estimating method executed by the emotion estimating apparatus 10 according to the embodiment. FIG. 5 is a schematic diagram illustrating an emotion output method executed by the emotion estimating apparatus 10 according to the embodiment. The functions of the emotion estimating apparatus 10 will now be described with reference to FIGS. 3 to 5.

As illustrated in FIG. 3, the emotion estimating apparatus 10 includes, an acquirer 20, an estimator 30, and an outputter 40 as functional blocks.

The acquirer 20 is a processor for acquiring physiology data and so on from the subject U. Specifically, the acquirer 20 acquires physiology data (corresponding to first data) and also acquires physiology data different from that physiology data or non-physiology data (corresponding to second data). The acquirer 20 includes a physiology data acquirer 21 and a data acquirer 22. The acquirer 20 may include one or more data acquires 22 (e.g., data acquires 2n).

The first data, the second data, and so on that the acquirer 20 acquires from the subject U are output to the estimator 30.

The physiology data acquirer 21 is a processor for acquiring the physiology data of the subject U from the subject U. The physiology data acquirer 21 acquires the physiology data of the subject U by using the physiology sensor included in the sensor 13. The physiology data acquirer 21 may also acquire the physiology data of the subject U, the data being held by another apparatus.

The data acquirer 22 is a processor for acquiring the physiology data or non-physiology data of the subject U from the subject U. The data acquirer 22 acquires the physiology data or non-physiology data of the subject U by using the physiology sensor or the non-physiology sensor included in the sensor 13. The data acquirer 22 may also acquire the physiology data or non-physiology data of the subject U, the data being held by another apparatus.

The physiology data acquirer 21 and the data acquirer 22 substantially simultaneously acquire the physiology data and the non-physiology data from the same subject U.

When there are a plurality of data acquires 22, each of the data acquires 22 independently acquires the physiology data or non-physiology data. Hence, at least one of a plurality of pieces of data acquired by the acquirer 20 is physiology data, and the other piece(s) of data is (are) physiology data or non-physiology data. For example, there is a case in which the acquirer 20 acquires one piece of physiology data and one piece of non-physiology data or a case in which the acquirer 20 acquires two pieces of physiology data (and does not acquire any non-physiology data).

The estimator 30 is a processor for estimating the emotion of the subject U which is estimated based on the data acquired by the acquirer 20. The estimator 30 includes an arousal-component calculator 31, a valence-component calculator 32, and an emotion estimator 33. The estimator 30 may also include a corrector 37.

The arousal-component calculator 31 is a processor for calculating an arousal level AR (see FIG. 4) indicating the degree of arousal of the subject U on the basis of the data acquired by the acquirer 20. More specifically, the arousal-component calculator 31 obtains each of the physiology data and the non-physiology data acquired by the physiology data acquirer 21 and the data acquirer 22 and calculates the arousal level AR on the basis of the obtained pieces of data. The arousal-component calculator 31 holds a parameter 34 that serves as a reference value for the physiology data and the non-physiology data, and calculates the arousal level AR by comparing the data acquired by the acquirer 20 with the reference value. The "physiology data and the non-physiology data acquired by the physiology data acquirer 21 and the data acquirer 22" as used herein may refer to data that does not include non-physiology data, as described above. The arousal level corresponds to a first value.

The arousal-component calculator 31 may also calculate the arousal level AR by excluding, of the physiology data and the non-physiology data, data determined to have a relatively small correlation with the arousal level.

For example, when the arousal-component calculator 31 calculates the arousal level AR on the basis of facial color which is physiology data, the arousal-component calculator 31 compares, for example, a luminance value of red of the facial color of the subject U, the facial color being acquired by the physiology data acquirer 21, with the reference value for the luminance value of red of the facial color, the reference value being held as the parameter 34. When the luminance value of red of the facial color of the subject U is equal to the reference value, the arousal level AR is calculated as being zero, and a higher arousal level AR is calculated for a larger luminance value of red of the facial color of the subject U (in other words, a smaller arousal level AR is calculated for a smaller luminance value).

The valence-component calculator 32 is a processor for calculating a valence level VA (see FIG. 4) indicating the degree of valence of the subject U on the basis of the data acquired by the acquirer 20. More specifically, the valence-component calculator 32 obtains each of the physiology data and the non-physiology data acquired by the physiology data acquirer 21 and the data acquirer 22 and calculates the valence level VA on the basis of the obtained pieces of data. The valence-component calculator 32 holds a parameter 35 that serves as a reference value for the physiology data and the non-physiology data, and the acquirer 20 calculates the valence level VA by comparing the acquired data with the reference value. The valence level corresponds to a second value.

The valence-component calculator 32 may calculate the valence level VA by excluding, of the physiology data and the non-physiology data, data determined to have a relatively small correlation with the valence level.

For example, when the valence-component calculator 32 calculates the valence level VA on the basis of a facial expression which is non-physiology data, the valence-component calculator 32 identifies, for example, a facial expression from feature points of facial parts from the subject U, the feature points being acquired by the data acquirer 22, and calculates the valence level VA for the identified facial expression on the basis of a predetermined association.

The emotion estimator 33 is a processor for estimating an emotion of the subject U on the basis of the arousal level AR calculated by the arousal-component calculator 31 and the valence level VA calculated by the valence-component calculator 32. For example, the emotion estimator 33 pre-holds, in a memory, a predetermined association (e.g., Russell's circumplex model illustrated in FIG. 1) between the arousal level and the valence level of people. This memory may be the memory 12 illustrated in FIG. 2 or may be a memory different from the memory 12 included in the emotion estimating apparatus 10. The different memory may be, for example, a storage device (which may also be referred to as an "external storage device") provided in a unit different from the emotion estimating apparatus 10. As long as the emotion estimating apparatus 10 has a configuration that can read information regarding the aforementioned predetermined association from the memory and can write information to the memory, the memory in which the predetermined association is stored may or may not be included in the emotion estimating apparatus 10.

The emotion estimator 33 estimates an emotion of the subject U by obtaining the arousal level AR calculated by the arousal-component calculator 31 and the valence level VA calculated by the valence-component calculator 32 and selecting an emotion that is associated with the obtained arousal level AR and valence level VA by the predetermined association.

When Russell's circumplex model is used as the predetermined association, the emotion estimator 33 plots points corresponding to the obtained arousal level AR and valence level VA against a plane with a horizontal axis indicating a valence level and a vertical axis indicating an arousal level and estimates, as the emotion of the subject U, an emotion allocated to the points in Russell's circumplex model (see FIG. 4).

The emotion estimator 33 holds a parameter 36 that serves as a reference for estimating an emotion on the basis of the arousal level AR and the valence level VA. The parameter 36 is, for example, a reference value representing a rate indicating which of the arousal level AR and the valence level VA is to be given a weight. On the basis of the arousal level AR and the valence level VA, the emotion estimator 33 estimates an emotion of the subject U with reference to the parameter 36.

The corrector 37 is a processor for correcting the parameter 34 held by the arousal-component calculator 31, the parameter 35 held by the valence-component calculator 32, and the parameter 36 held by the emotion estimator 33. The corrector 37 corrects the parameters 34, 35, and 36 by adjusting them on the basis of information regarding a physical characteristic of the subject U, more specifically, information such as the gender, nationality, age, skin color, or the like. For example, for calculating the arousal level AR on the basis of the heart rate, which is physiology data, the corrector 37 sets a reference value for the heart rate to a relatively small value when the subject U is a male. With this setting, the arousal-component calculator 31 calculates the arousal level of a male subject as being a larger value than the arousal level of a female subject, even when the heart rate is the same. This is because the heart rate of the male during a normal state is generally lower than the heart rate of the female during a normal state, and thus the male has a larger difference in the heart rate relative to a normal state when the heart rate is the same.

The estimator 30 outputs information indicating the estimated emotion to the outputter 40.

The outputter 40 is a processor for outputting information indicating the emotion estimated by the estimator 30. The outputter 40 includes a display unit 41. The display unit 41 is a processor for displaying the information indicating the emotion estimated by the estimator 30 on a display screen of the display device 14 as an image.

For example, the outputter 40 displays, on the display device 14, an image in which the data acquired by the acquirer 20 and the information indicating the emotion estimated by the estimator 30 are arranged, as illustrated in FIG. 5. The image illustrated in FIG. 5 includes an image 51 indicating the facial color of the subject U, the facial color being acquired by the physiology data acquirer 21 as physiology data, an image 52 indicating a facial expression of the subject U, the facial expression being acquired by the data acquirer 22 as non-physiology data, and an image 53 indicating the emotion of the subject U, the emotion being estimated by the estimator 30. The image 53 is one example of an image indicating the emotion of the subject U by using a point in a plane with two coordinate axes indicating a valence level and an arousal level. The image 53 may indicate at least one of the valence level and the arousal level. The image 53 may indicate a value representing the intensity of a predetermined emotion (e.g., happiness) of the subject U. The image 53 may also indicate at least one of the reliability of the arousal level of the subject U and the reliability of the valence level thereof.

A method for the output performed by the outputter 40 is not limited to the method illustrated in FIG. 5 and can take a variety of variations including, for example, outputting only the arousal level and outputting the intensity of a particular emotion. Some variations will be described below in detail.

The following description will be given of a specific configuration of the emotion estimating apparatus 10.

Figure 6:
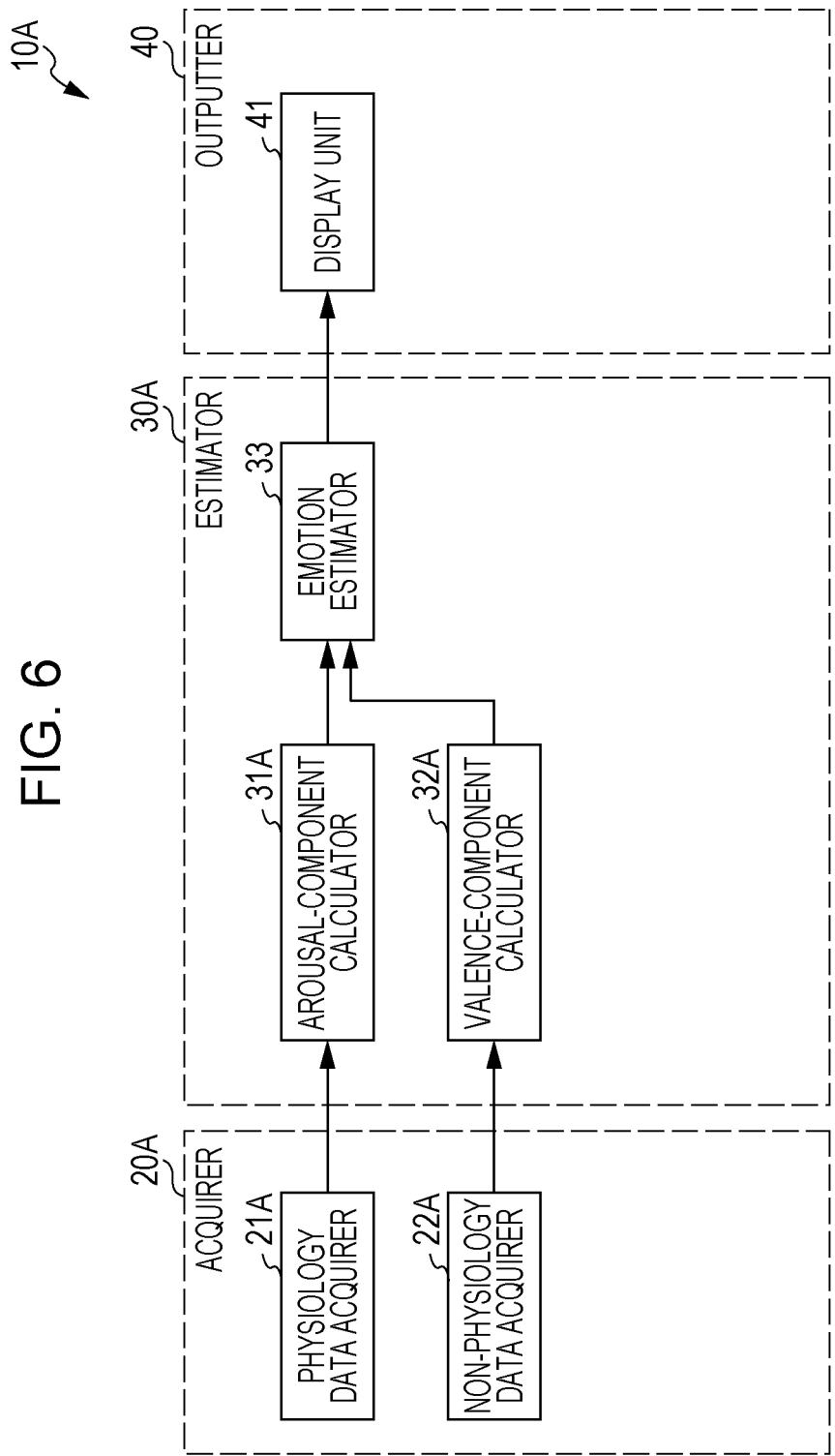
FIG. 6 is a block diagram illustrating a first specific example of the functional configuration of the emotion estimating apparatus according to the embodiment.

FIG. 6 is a block diagram illustrating an emotion estimating apparatus 10A, which is a first specific example of the functional configuration of the emotion estimating apparatus 10 according to the embodiment. Constituent elements that are the same as or similar to those in the emotion estimating apparatus 10 are denoted by the same reference numerals, and detailed descriptions thereof are not given. The same also applies to the description below.

As illustrated in FIG. 6, the emotion estimating apparatus 10A includes an acquirer 20A and an estimator 30A, which correspond to the acquirer 20 and the estimator 30, respectively, in the emotion estimating apparatus 10. Other constituent elements are substantially the same as those in the emotion estimating apparatus 10.

The acquirer 20A includes a physiology data acquirer 21A and a non-physiology data acquirer 22A.

The physiology data acquirer 21A is one specific example of the physiology data acquirer 21 in the emotion estimating apparatus 10 and is a processor for acquiring the physiology data of the subject U. The physiology data acquirer 21A supplies the acquired physiology data to an arousal-component calculator 31A.

The non-physiology data acquirer 22A is one specific example of the data acquirer 22 in the emotion estimating apparatus 10 and is a processor for acquiring the non-physiology data of the subject U. The non-physiology data acquirer 22A supplies the acquired non-physiology data to a valence-component calculator 32A.

The estimator 30A includes the arousal-component calculator 31A and the valence-component calculator 32A.

The arousal-component calculator 31A is one specific example of the arousal-component calculator 31 in the emotion estimating apparatus 10 and is a processor for calculating an arousal level on the basis of the physiology data acquired by the physiology data acquirer 21A. For calculating an arousal level, the arousal-component calculator 31A uses the physiology data acquired by the physiology data acquirer 21A and does not use the non-physiology data acquired by the non-physiology data acquirer 22A.

The valence-component calculator 32A is one specific example of the valence-component calculator 32 in the emotion estimating apparatus 10 and is a processor for calculating a valence level on the basis of the non-physiology data acquired by the non-physiology data acquirer 22A. For calculating a valence level, the valence-component calculator 32A uses the non-physiology data acquired by the non-physiology data acquirer 22A and does not use the physiology data acquired by the physiology data acquirer 21A.

The emotion estimating apparatus 10A can avoid an arousal level calculation using the non-physiology data having a relatively small correlation with the arousal level and a valence level calculation using the physiology data having a relatively small correlation with the valence level. As a result, there is an advantage in that an emotion of the subject U can be estimated based on data that are highly correlated with the arousal level and the valence level. In addition, since the configuration is simplified, there are also advantages in that the development cost of the apparatus is reduced and the maintenance and operating cost is reduced.

Figure 7:
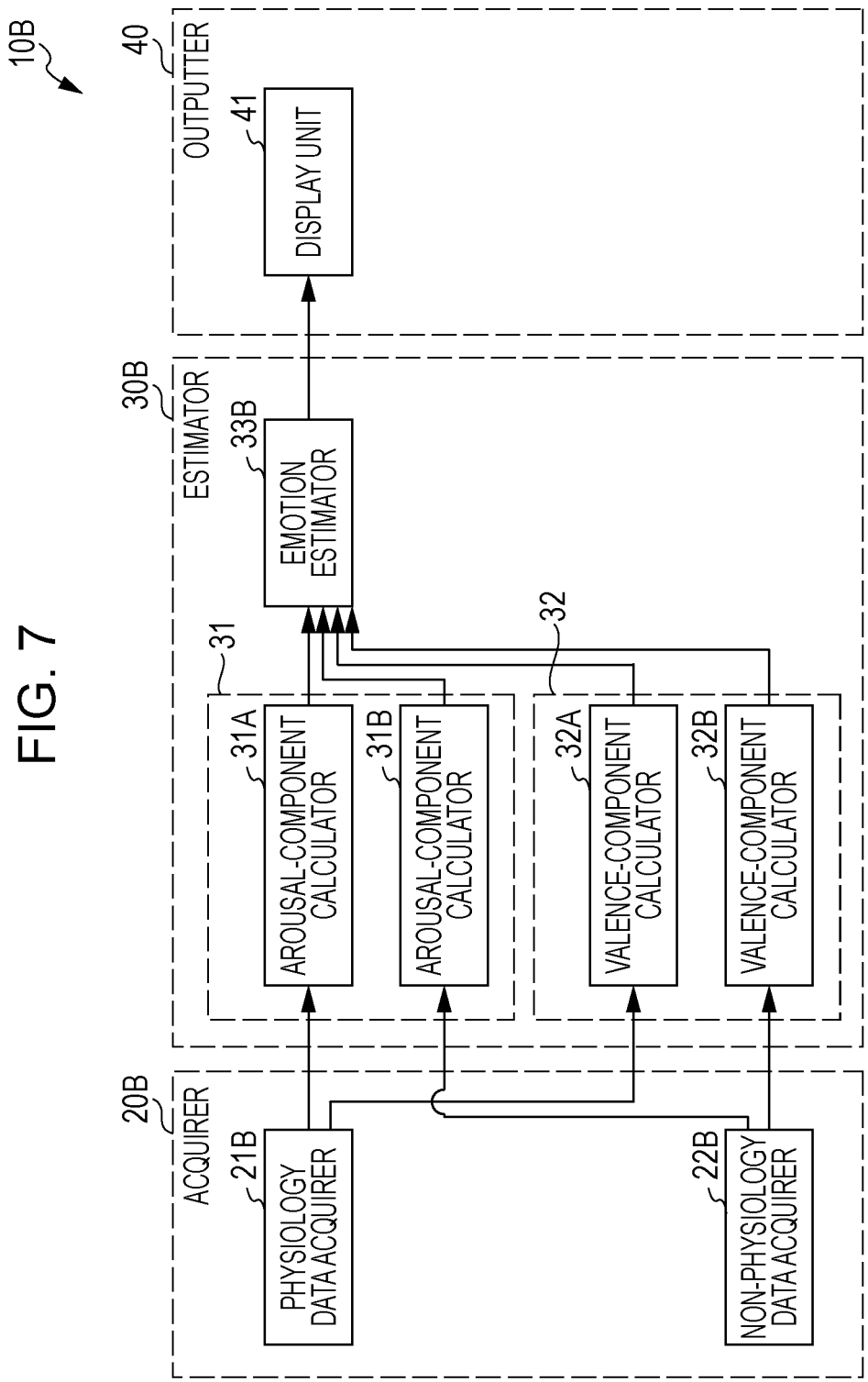
FIG. 7 is a block diagram illustrating a second specific example of the functional configuration of the emotion estimating apparatus according to the embodiment.
Figure 8:
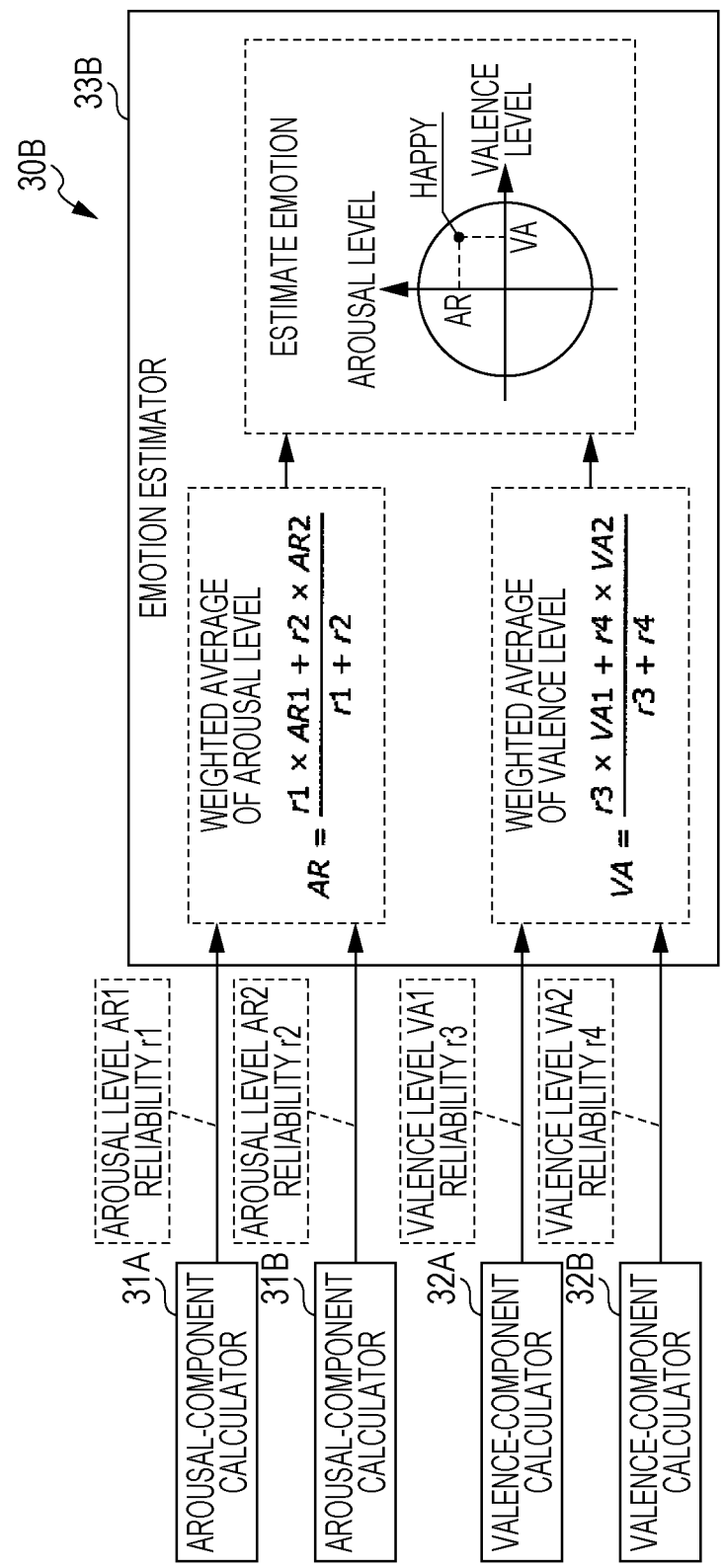
FIG. 8 is a block diagram illustrating emotion estimation processing in the second specific example of the functional configuration of the emotion estimating apparatus according to the embodiment.

FIG. 7 is a block diagram illustrating an emotion estimating apparatus 10B, which is a second specific example of the functional configuration of the emotion estimating apparatus 10 according to the embodiment. FIG. 8 is a block diagram illustrating emotion estimation processing performed by the emotion estimating apparatus 10B, which is the second specific example of the functional configuration of the emotion estimating apparatus 10 according to the embodiment.

As illustrated in FIG. 7, the emotion estimating apparatus 10B includes an acquirer 20B and an estimator 30B, which correspond to the acquirer 20 and the estimator 30, respectively, in the emotion estimating apparatus 10. Other constituent elements are substantially the same as those in the emotion estimating apparatus 10.

The acquirer 20B includes a physiology data acquirer 21B and a non-physiology data acquirer 22B.

The physiology data acquirer 21B is one specific example of the physiology data acquirer 21 in the emotion estimating apparatus 10 and is a processor for acquiring the physiology data of the subject U. The physiology data acquirer 21B supplies the acquired physiology data to both an arousal-component calculator 31A and a valence-component calculator 32A. As described above, the physiology data acquirer 21B differs from the physiology data acquirer 21 in the destination to which the acquired physiology data is supplied.

The non-physiology data acquirer 22B is one specific example of the data acquirer 22 in the emotion estimating apparatus 10 and is a processor for acquiring the non-physiology data of the subject U. The non-physiology data acquirer 22B supplies the acquired non-physiology data to both an arousal-component calculator 31B and a valence-component calculator 32B. As described above, the non-physiology data acquirer 22B differs from the data acquirer 22 in the element to which the acquired non-physiology data is supplied.

The estimator 30B includes the arousal-component calculators 31A and 31B and the valence-component calculators 32A and 32B. The arousal-component calculators 31A and 31B correspond to the arousal-component calculator 31 in the emotion estimating apparatus 10, and the valence-component calculators 32A and 32B correspond to the valence-component calculator 32 in the emotion estimating apparatus 10.

The arousal-component calculator 31A is a processor for calculating an arousal level (an arousal level AR1 in FIG. 8) on the basis of the physiology data acquired by the physiology data acquirer 21B. The arousal-component calculator 31A also calculates a reliability (a reliability r1 in FIG. 8) that is an indicator of correctness of emotion estimation based on the arousal level that is calculated.

Various methods are available as a method for calculating the reliability. For example, a low reliability may be calculated, as the amount of noise included in the physiology data acquired by the physiology data acquirer 21B increases. The reliabilities may be set according to the type of sensor 13 the physiology data acquirer 21B uses to acquire the physiology data from the subject U or may be freely set by the user.

The arousal-component calculator 31B is a processor for calculating an arousal level (an arousal level AR2 in FIG. 8) on the basis of the non-physiology data acquired by the non-physiology data acquirer 22B. The arousal-component calculator 31B also calculates a reliability (a reliability r2 in FIG. 8) of the arousal level that is calculated.

The valence-component calculator 32A is a processor for calculating a valence level (a valence level VA1 in FIG. 8) on the basis of the physiology data acquired by the physiology data acquirer 21B. The valence-component calculator 32A also calculates a reliability (a reliability r3 in FIG. 8) of the valence level that is calculated.

The valence-component calculator 32B is a processor for calculating a valence level (a valence level VA2 in FIG. 8) on the basis of the non-physiology data acquired by the non-physiology data acquirer 22B. The valence-component calculator 32B also calculates a reliability (a reliability r4 in FIG. 8) of the valence level that is calculated.

An emotion estimator 33B obtains the arousal levels from the respective arousal-component calculators 31B and 32B, obtains the valence levels from the respective valence-component calculators 32A and 32B, and estimates an emotion of the subject U.

Upon obtaining a plurality of arousal levels, the emotion estimator 33B calculates one arousal level on the basis of the plurality of arousal levels. There are various methods for calculating one arousal level on the basis of a plurality of arousal levels. Examples of the methods include a method for determining an average of the plurality of arousal levels, a method for determining a weighted average of the plurality of arousal levels by using the reliability of each arousal level as a weight, and a method for determining a median of the plurality of arousal levels.

FIG. 8 illustrates a method for determining a weighted average. Using the reliabilities r1 and r2 of the arousal levels AR1 and AR2, the emotion estimator 33B calculates one arousal level AR in accordance with:

$$AR=(r1 \times AR1+r2 \times AR2)/(r1+r2) \quad (1)$$

Also, using the reliabilities r3 and r4 of the valence levels VA1 and VA2, the emotion estimator 33B calculates one valence level VA in accordance with:

$$VA=(r3 \times VA1+r4 \times VA2)/(r3+r4) \quad (2)$$

The emotion estimator 33B estimates an emotion of the subject U by selecting an emotion that is associated with the calculated arousal level AR and valence level VA by a predetermined association (e.g., Russell's circumplex model).

Figure 9:
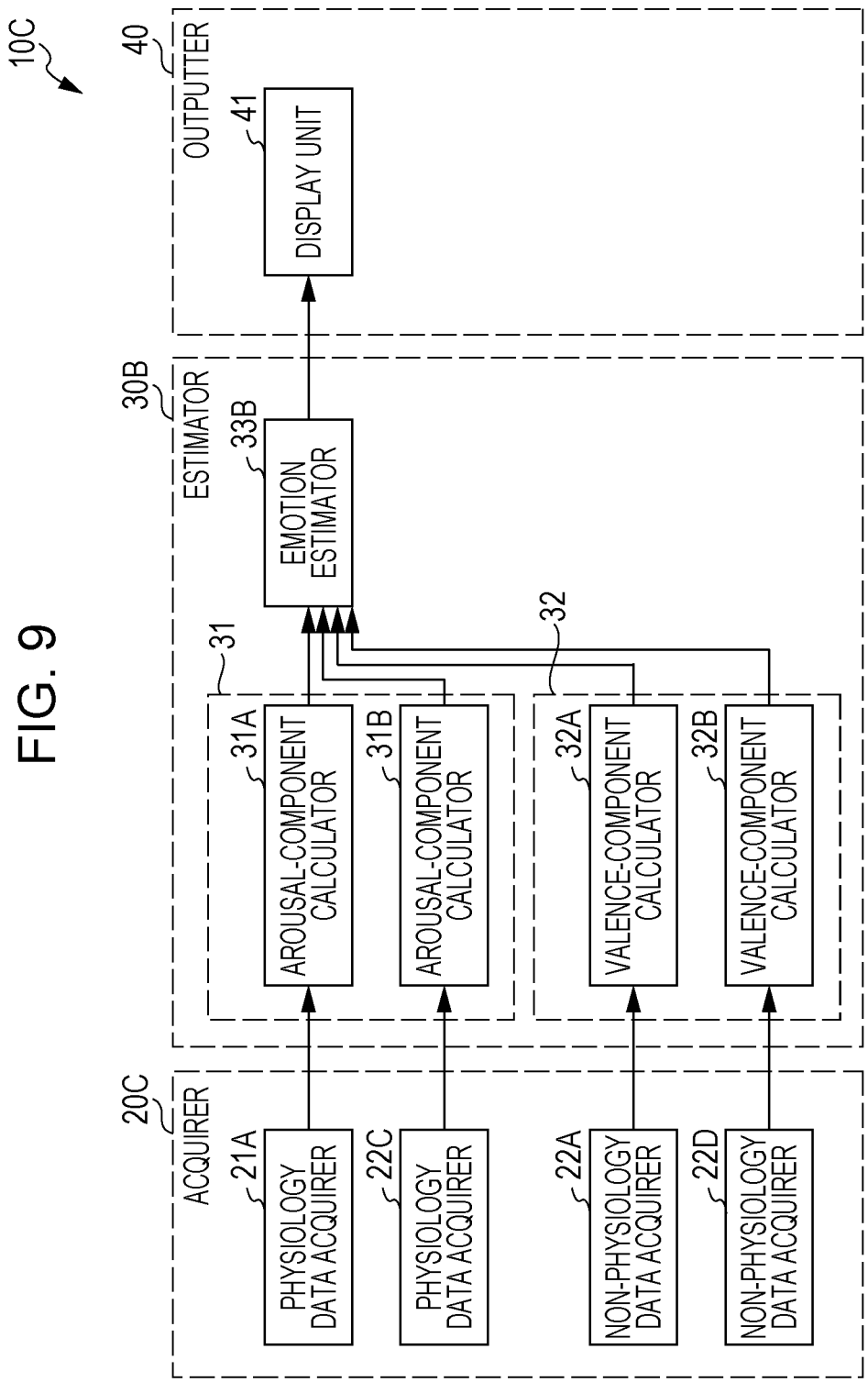
FIG. 9 is a block diagram illustrating a third specific example of the functional configuration of the emotion estimating apparatus according to the embodiment.

FIG. 9 is a block diagram illustrating an emotion estimating apparatus 10C, which is a third specific example of the functional configuration of the emotion estimating apparatus 10 according to the embodiment.

As illustrated in FIG. 9, the emotion estimating apparatus 10C includes an acquirer 20C and an estimator 30B, which correspond to the acquirer 20 and the estimator 30, respectively, in the emotion estimating apparatus 10. Other constituent elements are substantially the same as those in the emotion estimating apparatus 10.

The acquirer 20C includes physiology data acquires 21A and 22C and non-physiology data acquires 22A and 22D.

The physiology data acquirer 21A is one specific example of the physiology data acquirer 21 in the emotion estimating apparatus 10 and is a processor for acquiring the physiology data of the subject U. The physiology data acquirer 21A supplies the acquired physiology data to an arousal-component calculator 31A.

The physiology data acquirer 22C is one specific example of the data acquirer 22 in the emotion estimating apparatus 10 and is a processor for acquiring the physiology data of the subject U. The physiology data acquirer 22C supplies the acquired physiology data to an arousal-component calculator 31B.

The non-physiology data acquires 22A and 22D are specific examples of the data acquirer 22 in the emotion estimating apparatus 10 and are processors for acquiring the non-physiology data of the subject U. The non-physiology data acquirer 22A and 22D supplies the acquired non-physiology data to valence-component calculators 32A and 32B, respectively.

The estimator 30B estimates an emotion of the subject U on the basis of a plurality of arousal levels and a plurality of valence levels, as in the case of the emotion estimating apparatus 10B.

Figure 10:
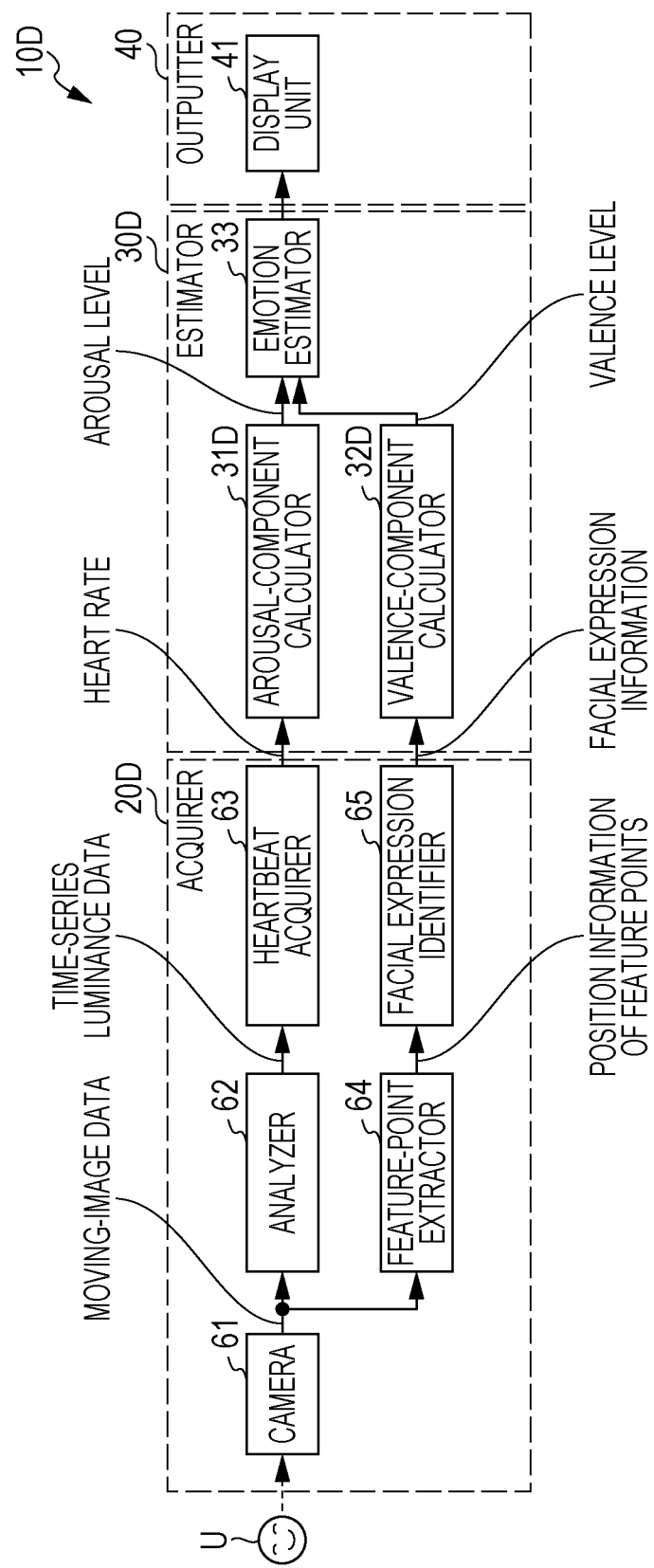
FIG. 10 is a block diagram illustrating a fourth specific example of the functional configuration of the emotion estimating apparatus according to the embodiment.

FIG. 10 is a block diagram illustrating an emotion estimating apparatus 10D, which is a fourth specific example of the functional configuration of the emotion estimating apparatus 10 according to the embodiment.

As illustrated in FIG. 10, the emotion estimating apparatus 10D includes an acquirer 20D and an estimator 30D, which correspond to more details of the acquirer 20A and the estimator 30A in the emotion estimating apparatus 10A.

The acquirer 20D includes a camera 61, an analyzer 62, a heartbeat acquirer 63, a feature-point extractor 64, and a facial expression identifier 65.

The camera 61 is an image capture device that captures a moving image of the face of the subject U to generate moving-image data. The camera 61 supplies the generated moving-image data to the analyzer 62 and the feature-point extractor 64.

The analyzer 62 is a processor for analyzing small changes in the color of the face of the subject U on the basis of the moving-image data generated by the camera 61. The analyzer 62 obtains the moving-image data generated by the camera 61 and extracts a face area of the subject U in the moving image. The analyzer 62 then generates time-series data indicating the colors of pixels included in the extracted face area. Since the facial color exhibits small changes based on a pulse wave (heartbeat), the time-series data has components that vary according to the pulse wave.

The heartbeat acquirer 63 is a processor for acquiring the heart rate of the subject U from the time-series data generated by the analyzer 62. The heartbeat acquirer 63 acquires the time-series data generated by the analyzer 62 and extracts the components that vary according to the pulse wave from the acquired time-series data by using a frequency filter or the like, to thereby acquire the heart rate.

The feature-point extractor 64 is a processor for extracting feature points of the face of the subject U on the basis of the moving-image data generated by the camera 61. The feature-point extractor 64 extracts a part, such as an eyebrow, an eye, the nose, or the mouth, of the subject U from the moving-image data and further extracts the positions of feature points (e.g., upper, lower, left, and right end points) of each part.

The facial expression identifier 65 is a processor for identifying a facial expression of the subject U on the basis of the part positions extracted by the feature-point extractor 64. For example, when the left and right end points of the mouth is located above a reference position, the facial expression identifier 65 identifies the facial expression of the subject U as being a smile.

The estimator 30D includes an arousal-component calculator 31D, a valence-component calculator 32D, and an emotion estimator 33.

The arousal-component calculator 31D compares the heart rate of the subject U, the heart rate being acquired by the heartbeat acquirer 63, with a reference value to calculate an arousal level of the subject U. For example, the arousal-component calculator 31D calculates the arousal level as being zero when the heart rate of the subject U, the heart rate being acquired by the heartbeat acquirer 63, is equal to the reference value, and the arousal-component calculator 31D calculates a higher arousal level, as the heart rate of the subject U acquired by the heartbeat acquirer 63 increases (in other words, the arousal-component calculator 31D calculates a lower arousal level, as the heart rate decreases).

The valence-component calculator 32D calculates a valence level on the basis of a facial expression of the subject U which is identified by the facial expression identifier 65. For example, when the facial expression of the subject U which is identified by the facial expression identifier 65 is a smile, the valence-component calculator 32D calculates a relatively large value for the valence level.

As described above, the emotion estimator 33 estimates an emotion of the subject U on the basis of the arousal level calculated by the arousal-component calculator 31D and the valence level calculated by the valence-component calculator 32D.

Processing performed by the emotion estimating apparatus 10 configured as described above will be described below.

Figure 11:
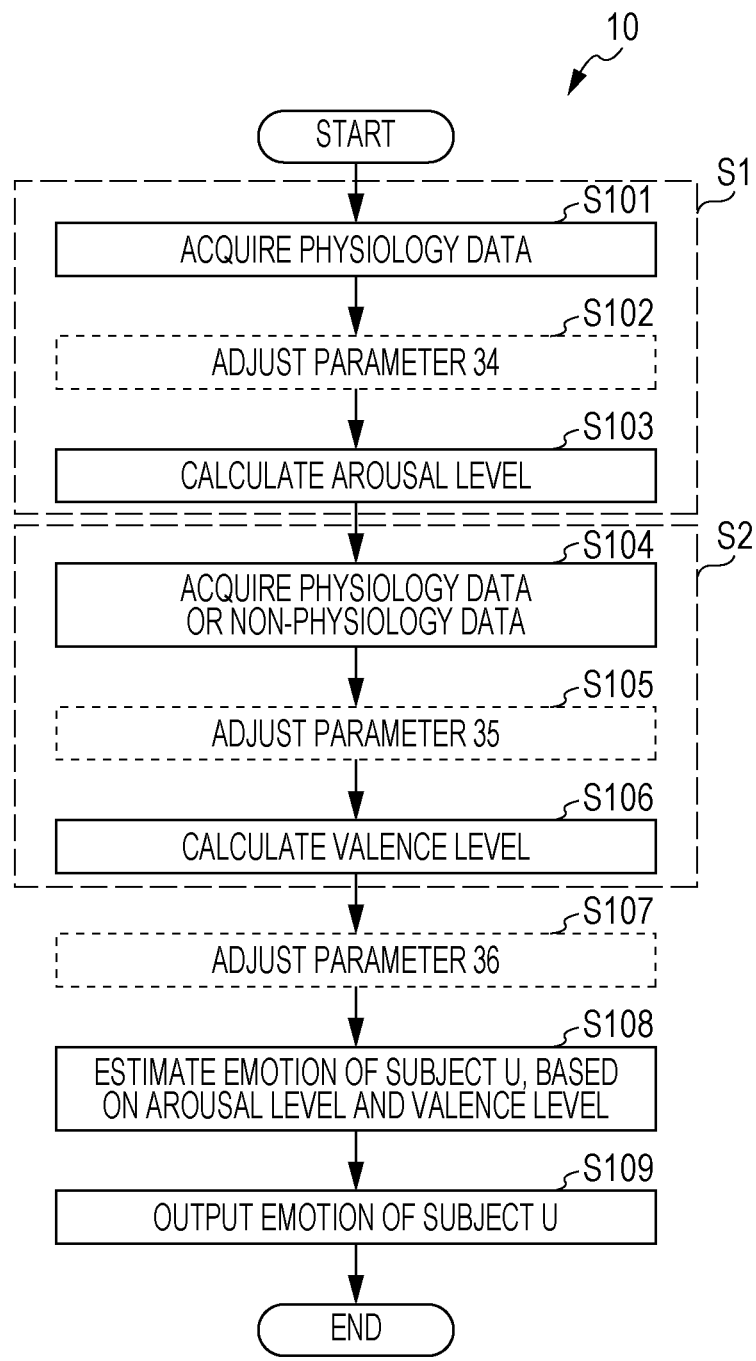
FIG. 11 is a flow diagram illustrating an estimation method by which the emotion estimating apparatus according to the embodiment estimates an emotion.

FIG. 11 is a flow diagram illustrating an estimation method by which the emotion estimating apparatus 10 according to the embodiment estimates an emotion.

First, the emotion estimating apparatus 10 acquires physiology data from the subject U in step S1 (steps S101 to S103) and acquires physiology data or non-physiology data from the subject U in step S2 (steps S104 to S106). Either of steps S1 and S2 may be performed earlier or steps S1 and S2 may be performed in parallel at the same time.

In step S101, the physiology data acquirer 21 acquires the physiology data of the subject U by using the physiology sensor.

In step S102, the corrector 37 adjusts the parameter 34 in the arousal-component calculator 31. Step S102 is not an essential processing step and does not necessarily have to be executed.

In step S103, the arousal-component calculator 31 calculates an arousal level on the basis of the physiology data acquired in step S101.

In step S104, by using the physiology sensor or non-physiology sensor, the data acquirer 22 acquires the physiology data or non-physiology data of the subject U.

In step S105, the corrector 37 adjusts the parameter 35 in the valence-component calculator 32. Step S105 is not an essential processing step and does not necessarily have to be executed.

In step S106, the valence-component calculator 32 calculates a valence level on the basis of the physiology data or non-physiology data acquired in step S104.

In step S107, the corrector 37 adjusts the parameter 36 in the emotion estimator 33. Step S107 is not an essential processing step and does not necessarily have to be executed.

In step S108, the emotion estimator 33 estimates an emotion of the subject U on the basis of the arousal level calculated in step S103 and the valence level calculated in step S106.

In step S109, the display unit 41 displays information indicating the emotion of the subject U, the emotion being estimated in step S108.

Through the above-described series of processes, the emotion estimating apparatus 10 estimates various emotions felt by the subject U, on the basis of the physiology data and non-physiology data acquired from the subject U.

The following description will be given of images and so on that the emotion estimating apparatus 10 displays on the display device 14.

Figure 12:
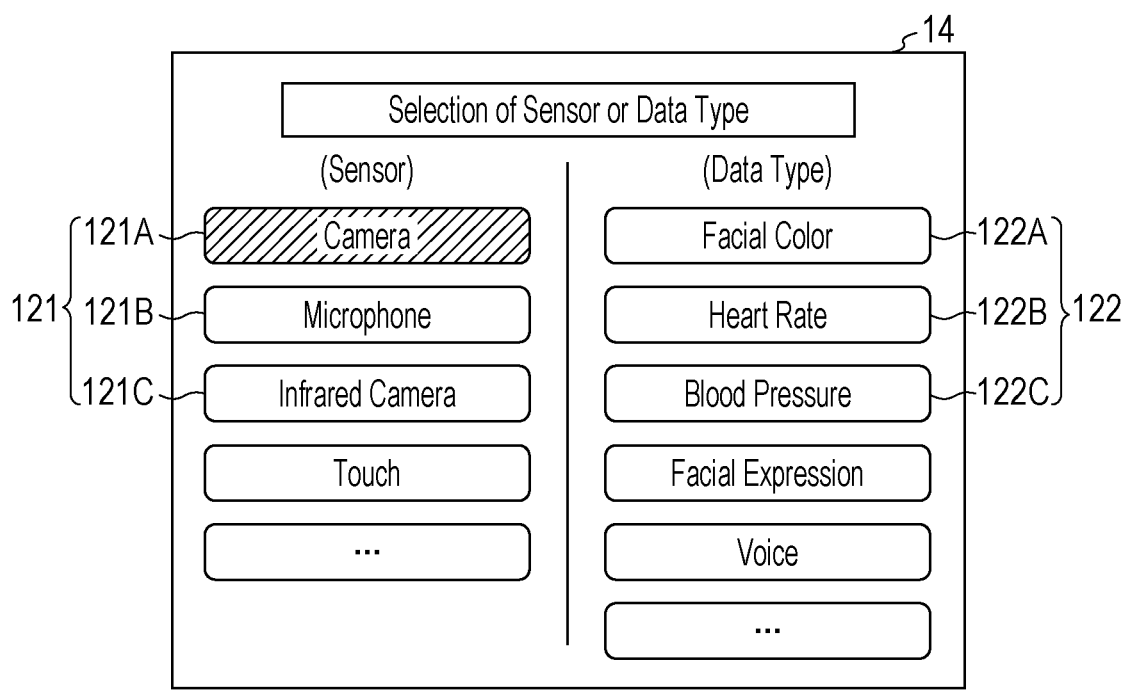
FIG. 12 is a schematic view of an image for receiving, from a user, a selection of a sensor that an acquirer according to the embodiment uses for data acquisition and a selection of data to be acquired.

FIG. 12 is a schematic view of an image for receiving, from the user, a selection of the sensor 13 that the acquirer 20 according to the embodiment uses for data acquisition and a selection of the data to be acquired.

The image illustrated in FIG. 12 is displayed on the display device 14 in order to receive, from the user, a selection of the sensor 13 that the acquirer 20 uses for data acquisition and a selection of the data to be acquired. The image includes a plurality of buttons 121 representing the sensors 13 and a plurality of buttons 122 representing data types.

More specifically, the buttons 121 representing the sensors 13 include buttons 121A, 121B, and 121C representing a camera, a microphone, and an infrared camera, which serve as the sensors 13. When the user operates (e.g., touches) any of the buttons representing the sensors 13 that the acquirer 20 uses for data acquisition, the operation input IF 15 receives the operation, and control is performed so that the acquirer 20 acquires data by using the sensor 13 corresponding to the operated button.

The buttons 122 representing the data types include, more specifically, buttons 122A, 122B, and 122C representing facial color, a heart rate, and a blood pressure, which are data types. When the user operates any of the buttons which represents the type of data to be acquired by the acquirer 20, the operation input IF 15 receives the operation, and control is performed so that the acquirer 20 acquires data of the type corresponding to the operated button.

The number of sensors 13 to be selected or the number of data types to be selected may be two or more, and the number of sensors 13 to be selected may have an upper limit or lower limit. When the sensors 13 and data types include items that are associated with each other, they may be selected in coordination with each other. For example, when the camera is selected as the sensor 13, the facial color and the heart rate, which are data types that can be acquired by the camera, may be automatically selected.

Figure 13:
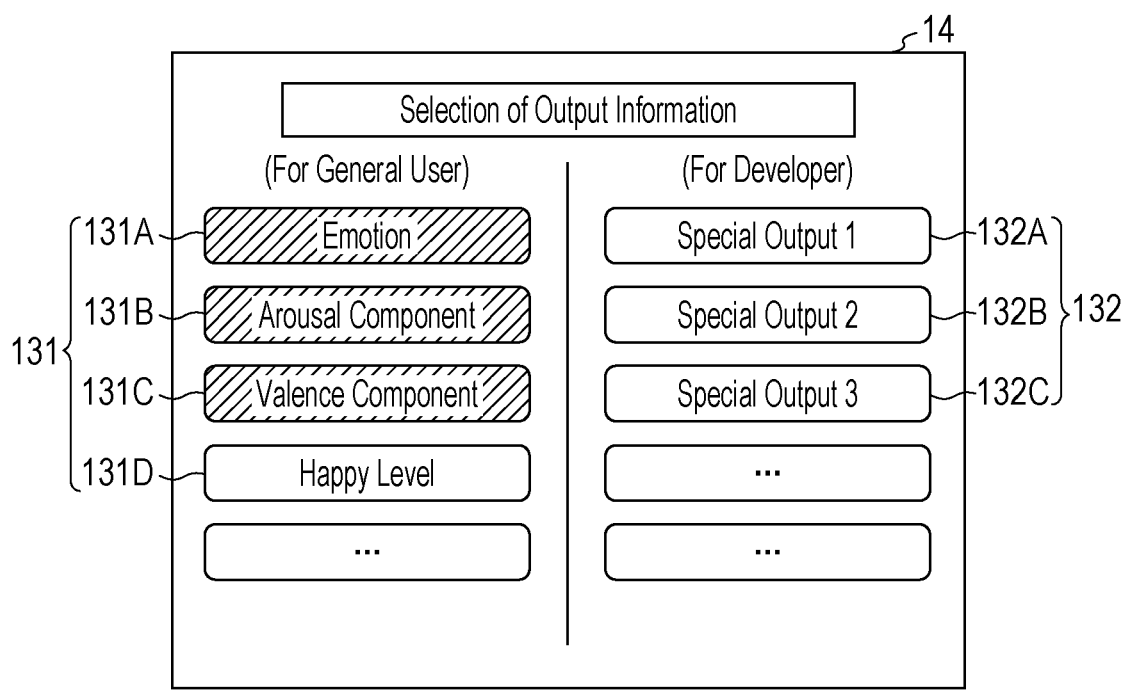
FIG. 13 is a schematic view of an image for receiving, from the user, a selection of information to be output from an outputter according to the embodiment.

FIG. 13 is a schematic view of an image for receiving, from the user, a selection of information to be output from the outputter 40 according to the embodiment. The image illustrated in FIG. 13 is displayed on the display device 14 in order to receive, from the user, a selection of information to be output from the outputter 40. This image includes a plurality of buttons 131 and a plurality of buttons 132 representing information to be output.

The buttons 131 are, for example, buttons for a general user, and, more specifically, includes buttons 131A, 131B, 131C, and, 131D respectively representing an emotion, an arousal level, a valence level, and a happy level. When the user operates any of the buttons which represents the information to be output from the outputter 40, the operation input IF 15 receives the operation, and control is performed so that the outputter 40 outputs the information corresponding to the operated button. For example, when the user operates the button 131A, the outputter 40 outputs the estimated emotion of the subject U. Also, when the user operates the button 131B, the outputter 40 outputs the arousal level of the subject U.

The buttons 132 are, for example, buttons for a developer and include, more specifically, buttons 132A, 132B, and 132C respectively representing three special outputs 1, 2, and 3. The special outputs are output methods provided for adjusting, on a trial basis, a method for calculating an arousal level and a valence level. When the user operates any of the buttons which represents the information to be output from the outputter 40, the operation input IF 15 receives the operation, and control is performed so that the outputter 40 outputs the information corresponding to the operated button.

A plurality of pieces of information may selected to be output, and the number of sensors 13 to be selected may have an upper limit or a lower limit.

Figure 14:
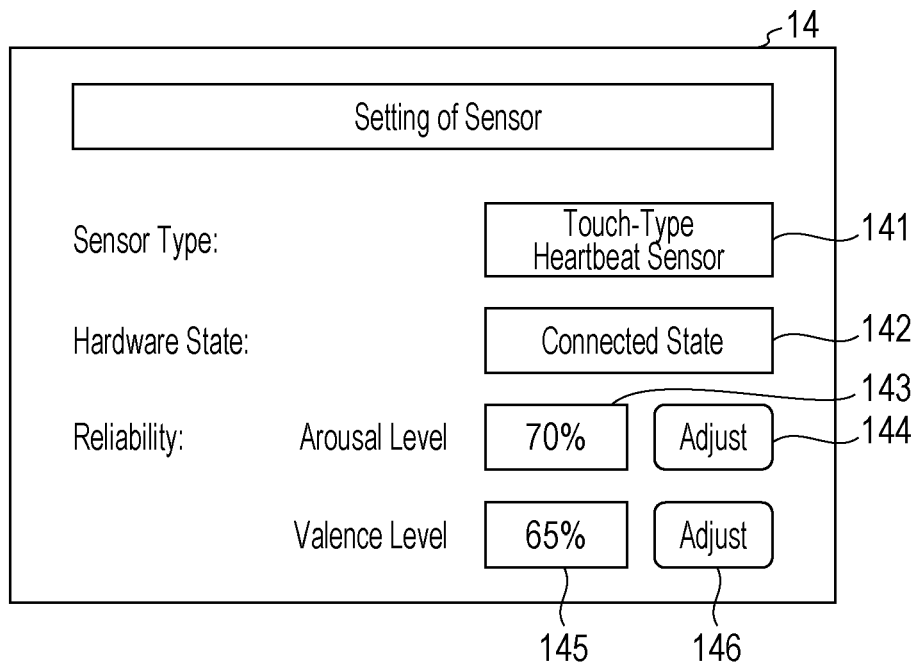
FIG. 14 is a schematic view of an image for receiving, from the user, settings of the sensor according to the embodiment.

FIG. 14 is a schematic view of an image for receiving, from the user, settings of the sensor 13 according to the embodiment. The image illustrated in FIG. 14 is displayed on the display device 14 in order to receive, from the user, settings regarding the type of sensor 13 and so on. This image includes a button 141 indicating the type of sensor 13, a display area 142 indicating the state of the hardware of the sensor 13, a display area 143 indicating the reliability of an arousal level, a button 144 for adjusting the reliability of the arousal level, a display area 145 indicating the reliability of a valence level, and a button 146 for adjusting the reliability of the valence level.

For changing the type of sensor 13, the user operates the button 141 and then performs an operation for entering a post-change type of sensor 13. the operation is received by the operation input IF 15, and control is performed so that the type of sensor 13 is changed, and a character string displayed on the button 141 is changed to the changed type of sensor 13.

The display area 142 is a display area in which information indicating whether or not the sensor 13 is appropriately connected to the emotion estimating apparatus 10 is displayed. When the sensor 13 is appropriately connected, "connected state" is displayed, and when the sensor 13 is not appropriately connected, "disconnected state" is displayed.

The display areas 143 and 145 display the reliabilities of the arousal level and the valence level, respectively. When the user adjusts one of the reliabilities, he or she operates the corresponding button 144 or 146 and then performs an operation for changing the reliability.

Figure 15:
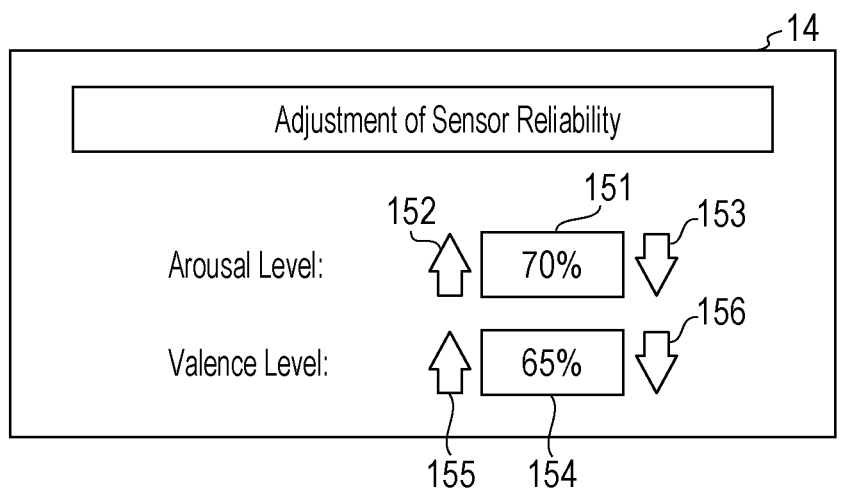
FIG. 15 is a schematic view of an image for receiving, from the user, an adjustment of the reliability of the sensor according to the embodiment.

FIG. 15 is a schematic view of an image for receiving, from the user, an adjustment of the reliability of the sensor 13 according to the embodiment. The image illustrated in FIG. 15 is displayed on the display device 14 in order to receive, from the user, settings regarding adjustment of the reliability (specifically, an increase or reduction in the reliability) of the sensor 13. The image is displayed, for example, when the operation input IF 15 receives the user's operation on the button 144 or 146 illustrated in FIG. 14.

The image includes display areas 151 and 154 in which the reliability of the arousal level and the reliability of the valence level are displayed. The image further includes buttons 152 and 155 for increasing the respective reliabilities of the arousal level and the valence level and buttons 153 and 156 for reducing the respective reliabilities of the arousal level and the valence level.

For increasing or reducing the arousal level reliability of the sensor 13, the user operates the corresponding button 152 or 153. When the operation input IF 15 receives the operation, the arousal level reliability of the sensor 13 is increased or reduced in accordance with the operation, and a numerical value representing the arousal level displayed on the display area 151 is increased or reduced. As described above, the emotion estimating apparatus 10 can perform adjustment while presenting a numerical value representing the reliability of the valence level to the user. Since a description similar to the above description also applies to the valence level, the description thereof is not given hereinafter.

Figure 16:
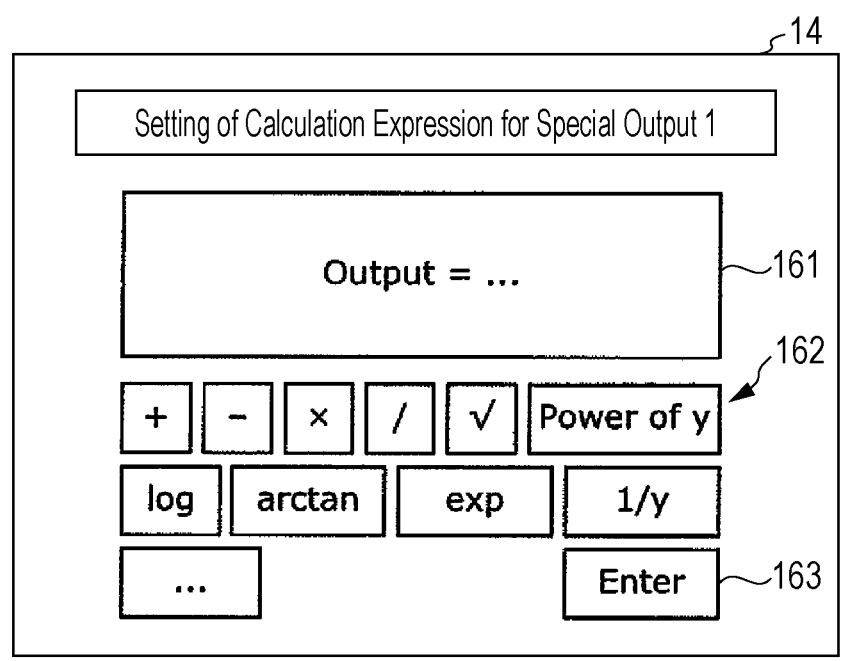
FIG. 16 is a schematic view of an image for setting a calculation expression regarding output information according to the embodiment.

FIG. 16 is a schematic view of an image for setting a calculation expression regarding output information according to the embodiment. The image illustrated in FIG. 16 is displayed on the display device 14 in order to receive, from the user, settings of a calculation expression for a special output, which is one piece of output information. This image is displayed, for example, when the operation input IF 15 receives the user's operation on the button 132A in FIG. 13 or the like.

The image includes a display area 161 for a calculation expression, buttons 162 for entering operators, and a button 163 for determining the calculation expression. When the user's operation on any of the buttons 162 is performed, the operation input IF 15 receives the operation, and the calculation expression displayed on the display area 161 is updated. When the user's operation on the button 163 is performed, the operation input IF 15 receives the operation, and the calculation expression displayed on the display area 161 is determined to be a calculation expression for special output 1.

For modifying the contents of the special output, the user can modify the calculation expression by viewing the calculation expression displayed on the display area 161 and operating the buttons 162.

Figure 17:
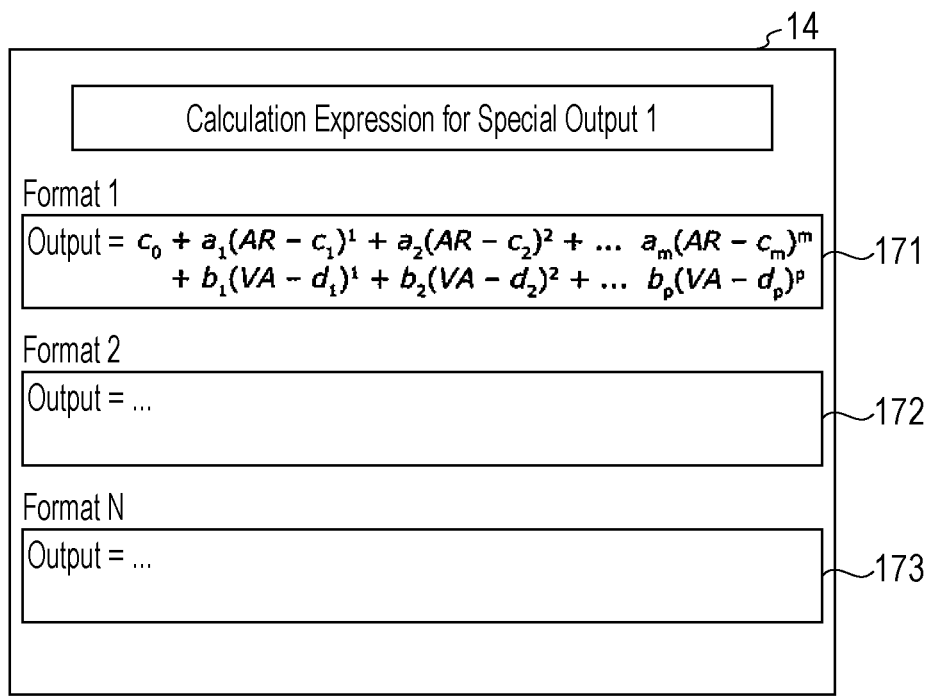
FIG. 17 is a schematic view of an image for checking a calculation expression regarding output information according to the embodiment.

FIG. 17 is a schematic view of an image for checking a calculation expression regarding output information according to the embodiment. The image illustrated in FIG. 17 is displayed on the display device 14 in order for the user to view a calculation expression for a special output, which is one piece of output information. This image is displayed, for example, when the operation input IF 15 receives the user's operation on the button 163 in FIG. 16.

The image includes display areas 171, 172, and 173 respectively showing calculation expressions for three special outputs. For example, calculation expressions that the user set on the basis of the image illustrated in FIG. 16 are displayed in the display areas 171, 172, and 173. By viewing the calculation expressions for the three special outputs as a single image, the user can efficiently recognize the relationship among the calculation expressions and can find a point to be modified in the calculation expressions.

Figure 18:
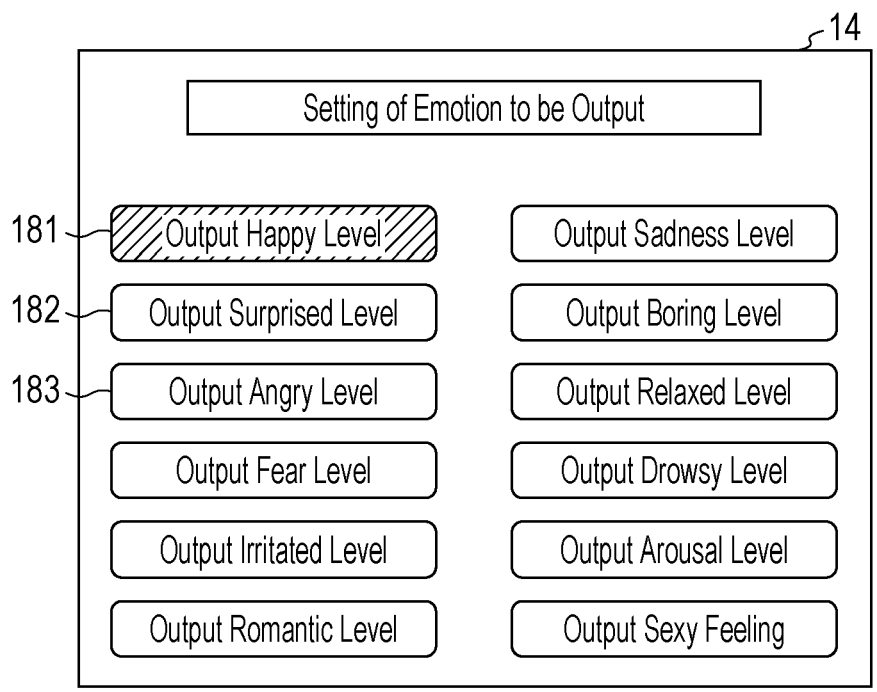
FIG. 18 is a schematic view of an image for selecting an output of information indicating an emotion according to the embodiment.

FIG. 18 is a schematic view of an image for selecting an output of information indicating an emotion according to the embodiment. The image illustrated in FIG. 18 is displayed on the display device 14 in order for the emotion estimating apparatus 10 to set information to be output as an estimated emotion.

This image includes buttons 181, 182, and 183 representing candidates of information that the emotion estimating apparatus 10 outputs as an estimated emotion. The buttons 181, 182, and 183 are given corresponding character strings indicating emotions. When the user performs an operation on any of the buttons, the operation input IF 15 receives the operation, and control is performed so as to perform switching as to whether or not the emotion corresponding to the operated button is to be output as an estimated emotion. For example, when a determination that the happy level is to be output, the surprised level is to be output, and the angry level is not to be output is made upon button-operation performed by the user, the estimator 30 is permitted to output information indicating "happy" and "surprised" as the emotions of the subject U and is not permitted to output information indicating "angry".

The user can also limit the emotions to be output to some of the emotions. This offers an advantage in that the user can obtain, for example, only an estimation result needed by the subject U or can prevent an estimation result he or she doesn't want other people to see from being output when the user is the subject U and there is a possibility that other people see the estimation result.

Figure 19:
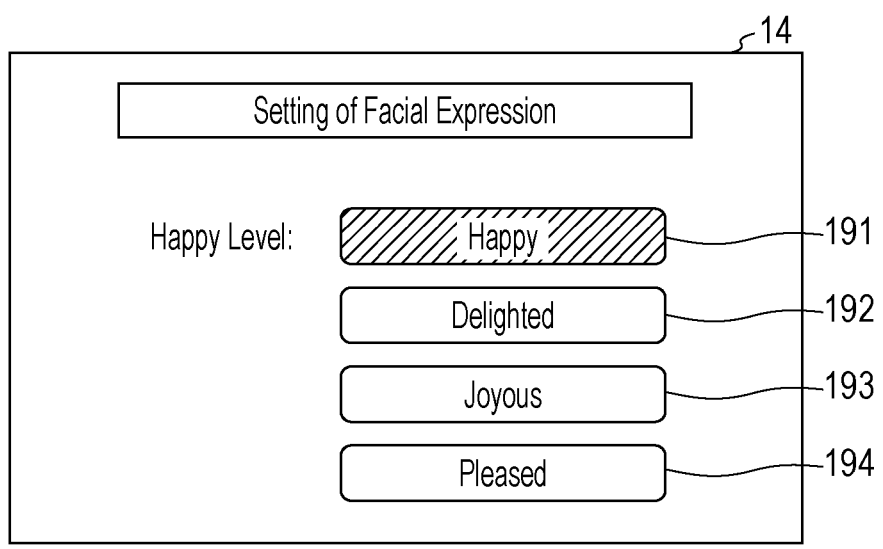
FIG. 19 is a schematic view of an image for setting a representation of information indicating an emotion according to the embodiment.

FIG. 19 is a schematic view of an image for setting a representation of information indicating an emotion according to the embodiment. The image illustrated in FIG. 19 is displayed on the display device 14 in order for the emotion estimating apparatus 10 to set a representation of information to be output as an estimated emotion.

This image includes buttons 191, 192, 193, and 194 representing candidates of a representation of information that the emotion estimating apparatus 10 outputs as an estimated emotion. Each of the buttons 191, 192, 193, and 194 is given a character string of a representation indicating an emotion of happiness or an emotion similar thereto. When the user performs an operation on any of the buttons, the operation input IF 15 receives the operation, and control is performed so that the outputter 40 outputs information using the representation corresponding to the operated button. For example, when the user performs a button operation to select the button 191 "happy", a representation "happy" is output during output of the emotion of happiness.

Figure 20:
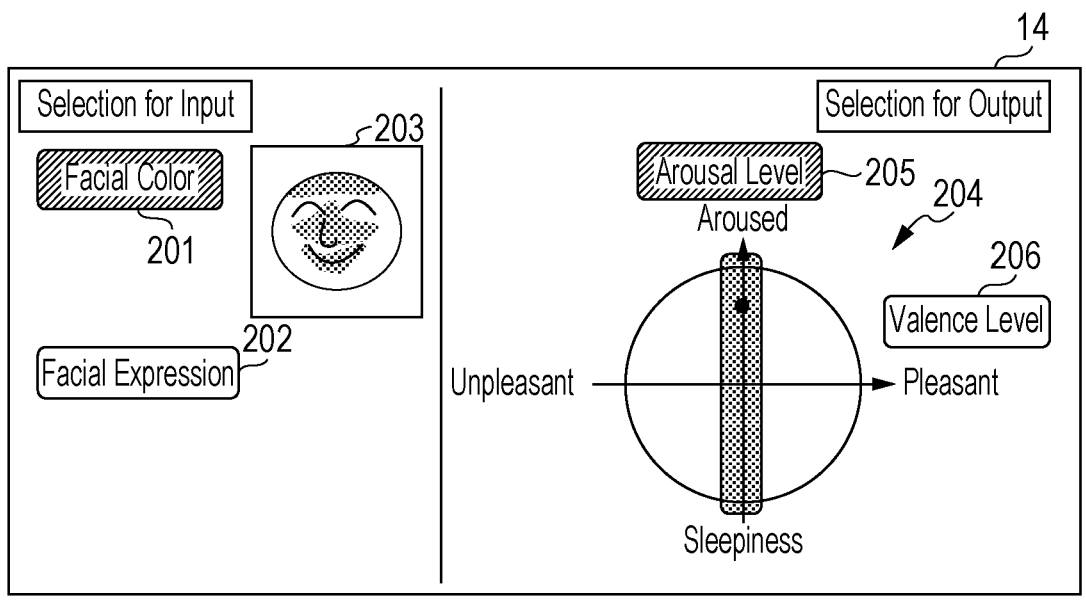
FIG. 20 is a schematic view of a first example of an image including information indicating an emotion estimated by an estimator according to the embodiment.

FIG. 20 is a schematic view of a first example of an image including information indicating an emotion estimated by the estimator 30 according to the embodiment.

The image illustrated in FIG. 20 is displayed on the display device 14 in order to set information to be output as an emotion estimated by the estimator 30.

This image includes, at its left side, an image regarding an input and includes, at its right side, information regarding an output.

The left side in the image illustrated in FIG. 20 includes a button 201 for selecting whether or not "facial color", which is physiology data, is to be acquired from the subject U, a button 202 for selecting whether or not "facial expression", which is non-physiology data, is to be acquired from the subject U, and an image 203 showing data acquired from the subject U. When the user operates any of the above-described buttons which represents the data to be acquired by the acquirer 20, the operation input IF 15 receives the operation, and control is performed so that the acquirer 20 acquires the data corresponding to the operated button. FIG. 20 illustrates a state in which control is performed so that the acquirer 20 acquires "facial color", and the color of the button 201 is shown in dark color. Also, the image 203 shows the facial color actually acquired from the subject U.

The right side in the image illustrated in FIG. 20 includes an image 204 representing the emotion of the subject U, the emotion being estimated by the estimator 30, a button 205 for selecting whether or not the arousal level is to be output, and a button 206 for selecting whether or not the valence level is to be output. FIG. 20 illustrates a state in which the estimator 30 estimates an emotion by using the arousal level and without using the valence level, and the button 205 is shown in dark color. in the image 204, the emotion estimated by the estimator 30 is shown using only the arousal level.

Thus, the user or the subject U can intuitively recognize an estimation result of the emotion of the subject U by viewing a single image in which the data acquired from the subject U and the emotion estimated based on the data are arranged.

Figure 21:
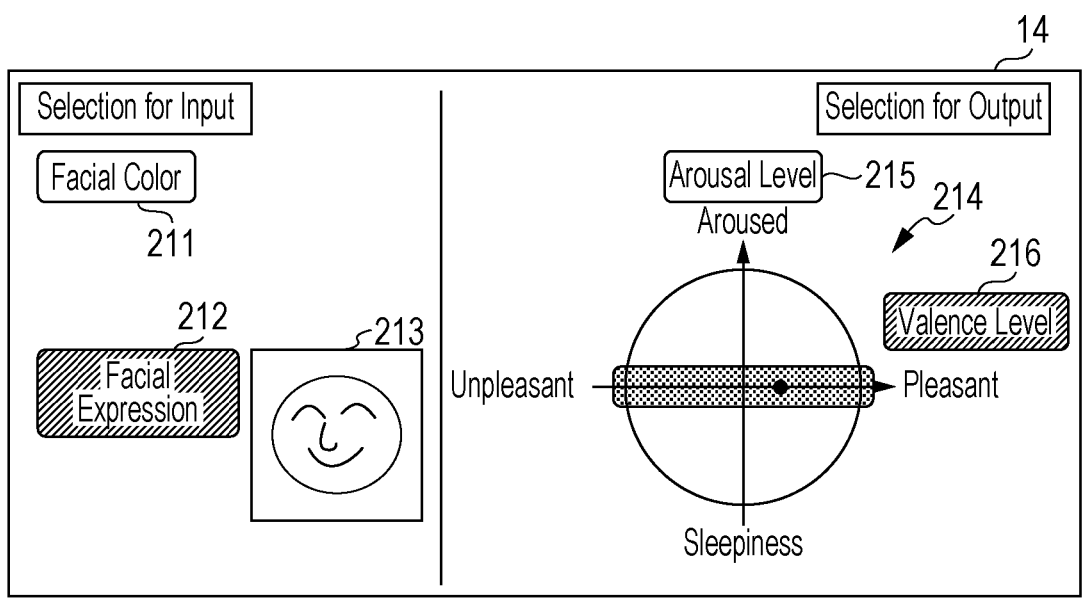
FIG. 21 is a schematic view of a second example of the image including the information indicating the emotion estimated by the estimator according to the embodiment.

FIG. 21 is a schematic view of a second example of an image including information indicating an emotion estimated by the estimator 30 according to the embodiment. The overall configuration of the image illustrated in FIG. 21 is substantially the same as that of the image illustrated in FIG. 20, and differs from that of the image illustrated in FIG. 20 in information acquired from the subject U and information to be output.

The left side in the image illustrated in FIG. 21 includes a button 211 for selecting whether or not "facial color" is to be acquired from the subject U, a button 212 for selecting whether or not "facial expression" is to be acquired from the subject U, and an image 213 showing the acquired data, as in the image illustrated in FIG. 20. FIG. 21 illustrates a state in which the acquirer 20 is controlled so as to acquire "facial expression", and the color of the button 212 is shown in dark color. Also, the image 213 shows the facial color actually acquired from the subject U.

The right side in the image illustrated in FIG. 21 includes an image 214 representing the emotion of the subject U, a button 215 for selecting whether or not the arousal level is to be output, and a button 216 for selecting whether or not the valence level is to be output. FIG. 21 illustrates a state in which the estimator 30 estimates an emotion by using the valence level and without using the arousal level, and the button 216 is shown in dark color. In the image 214, the emotion estimated by the estimator 30 is shown using only the valence level.

Figure 22:
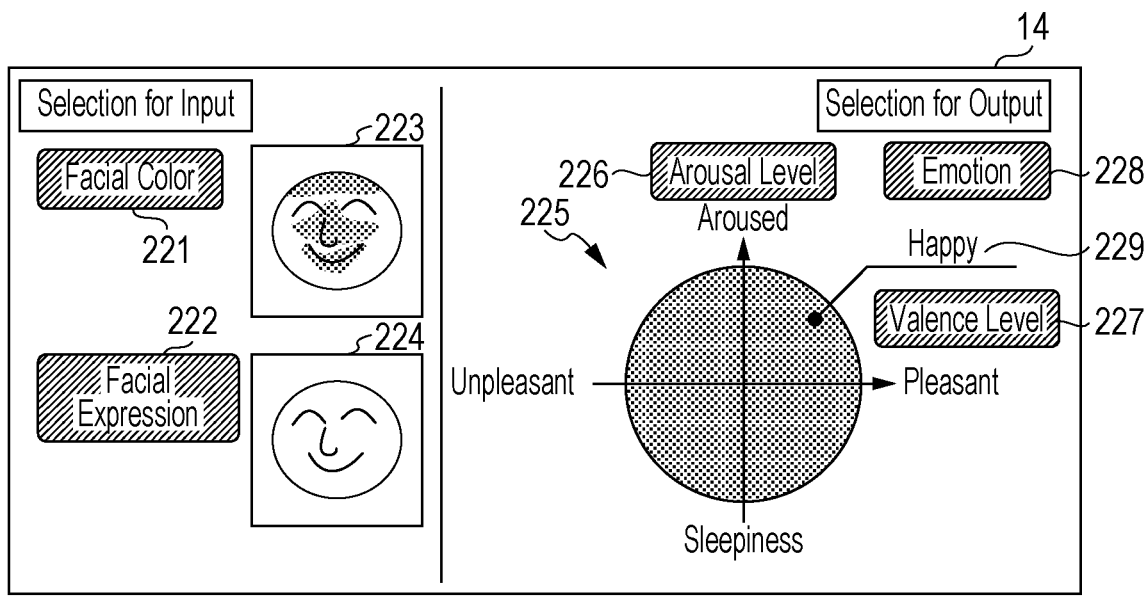
FIG. 22 is a schematic view of a third example of the image including the information indicating the emotion estimated by the estimator according to the embodiment.

FIG. 22 is a schematic view of a third example of an image including information indicating an emotion estimated by the estimator 30 according to the embodiment. The overall configuration of the image illustrated in FIG. 22 is substantially the same as that of the image illustrated in FIG. 20, and differs from that of the image illustrated in FIG. 20 in information acquired from the subject U and information to be output.

The left side in the image illustrated in FIG. 22 includes a button 221 for selecting whether or not "facial color" is to be acquired from the subject U and a button 222 for selecting whether or not "facial expression" is to be acquired from the subject U, as in the image illustrated in FIG. 20, and includes images 223 and 224 showing acquired data. FIG. 22 illustrates a state in which the acquirer 20 is controlled so as to acquire "facial color" and "facial expression", and the colors of the button 221 and 222 are shown in dark color. Also, the images 223 and 224 show the facial color and facial expression, respectively, actually acquired from the subject U.

The right side in the image illustrated in FIG. 22 includes an image 225 representing the emotion of the subject U, a button 226 for selecting whether or not the arousal level is to be output, a button 227 for selecting whether or not the valence level is to be output, a button 228 for selecting whether or not the estimated emotion is to be output, and a character string 229 representing the estimated emotion. FIG. 22 illustrates a state in which the estimator 30 estimates an emotion by using the arousal level and the valence level, and the buttons 226 and 227 are shown in dark color. In the image 225, the emotion estimated by the estimator 30 is shown using the arousal level and the valence level.

In addition, FIG. 22 shows a state in which the estimated emotion is output, and the button 228 is shown in dark color. In this case, the character string 229 representing the estimated emotion is shown. The button 228 may be displayed only when outputting both the arousal level and the valence level is selected with the buttons 226 and 227. This is because, when one of the arousal level and the valence level is to be output, showing an emotion estimated from both the arousal level and the valence level is not appropriate.

Figure 23:
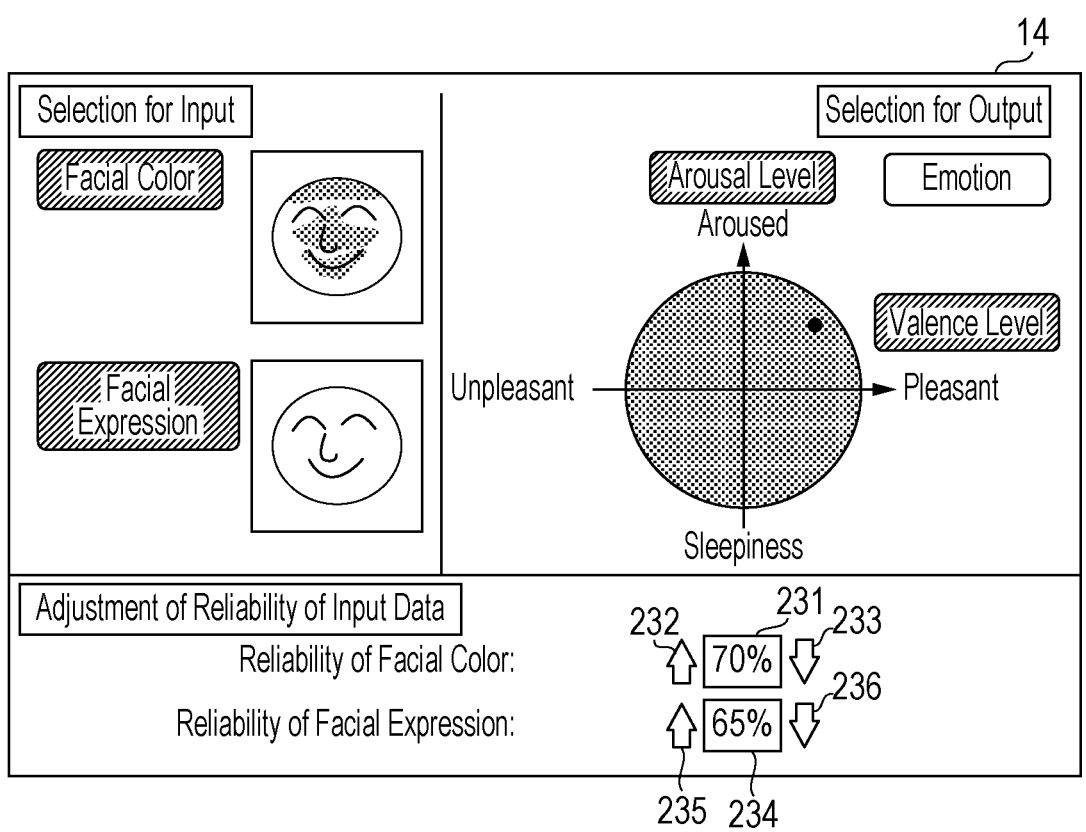
FIG. 23 is a schematic view of a fourth example of the image including the information indicating the emotion estimated by the estimator according to the embodiment.

FIG. 23 is a schematic view of a fourth example of the image including the information representing the emotion estimated by the estimator 30 according to the embodiment. The upper portion in the image illustrated in FIG. 23 is substantially the same as the image illustrated in FIG. 22. The lower portion in the image illustrated in FIG. 23 includes an image for setting the reliabilities of physiology data and non-physiology data (input data) acquired by the acquirer 20.

The image for setting the reliabilities of the input data includes a display area 231 in which the reliability of "facial color", which is physiology data, acquired by the acquirer 20 is displayed, and a display area 234 in which the reliability of "facial expression", which is non-physiology data, acquired by the acquirer 20 is displayed, and buttons 232, 233, 235, and 236 for adjusting the reliabilities. Since a method for adjusting the reliabilities are the same as or similar to that in FIG. 15, a description thereof is not given hereinafter.

Figure 24:
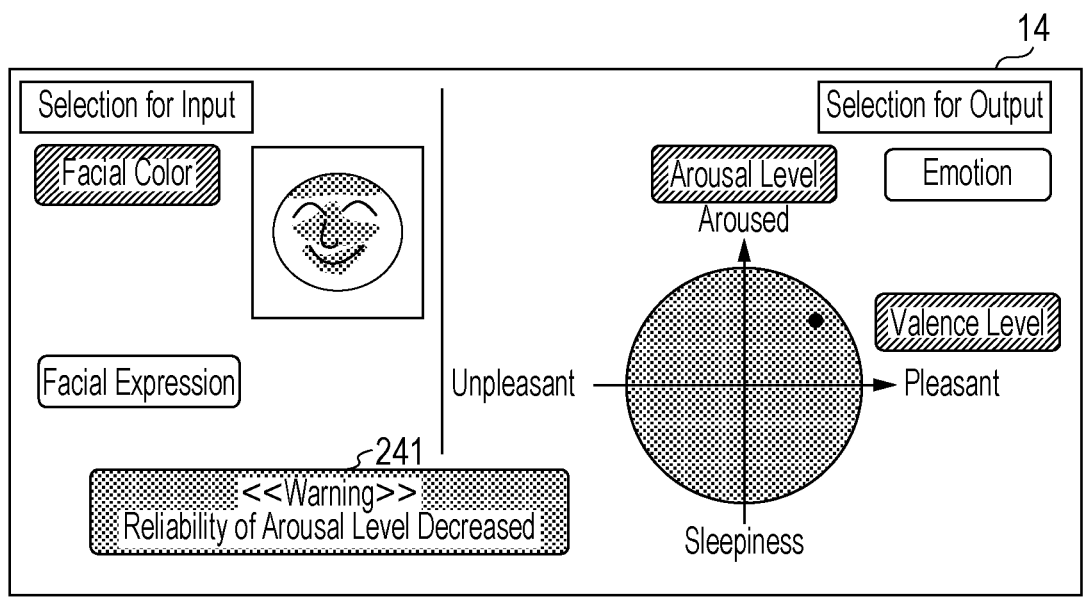
FIG. 24 is a schematic view of a fifth example of the image including the information indicating the emotion estimated by the estimator according to the embodiment.

FIG. 24 is a schematic view of a fifth example of the image including the information representing the emotion estimated by the estimator 30 according to the embodiment. The overall configuration of the image illustrated in FIG. 24 is substantially the same as the image illustrated in FIG. 20, and differs from that of the image illustrated in FIG. 20 in information acquired from the subject U and information to be output.

The left side in the image illustrated in FIG. 24 is substantially the same as that in FIG. 20. That is, FIG. 24 shows a state in which the acquirer 20 is controlled so as to acquire "facial color".

The right side in the image illustrated in FIG. 24 shows a state in which the estimator 30 estimates an emotion by using the arousal level and the valence level and also displays information representing an estimated emotion.

The image illustrated in FIG. 24 also includes an image 241 for issuing a warning indicating that the reliability of the valence level estimated from the "facial color", which is physiology data, is low.

As described above, the outputter 40 displays an emotion estimated from the arousal level and the valence level, and also, when at least one of the reliability of the arousal level and the reliability of the valence level is lower than a predetermined value, the outputter 40 displays an image to that effect. Upon viewing the image, the user or the subject U can determine that the emotion that is output together with the warning is not so correct.

Figure 25:
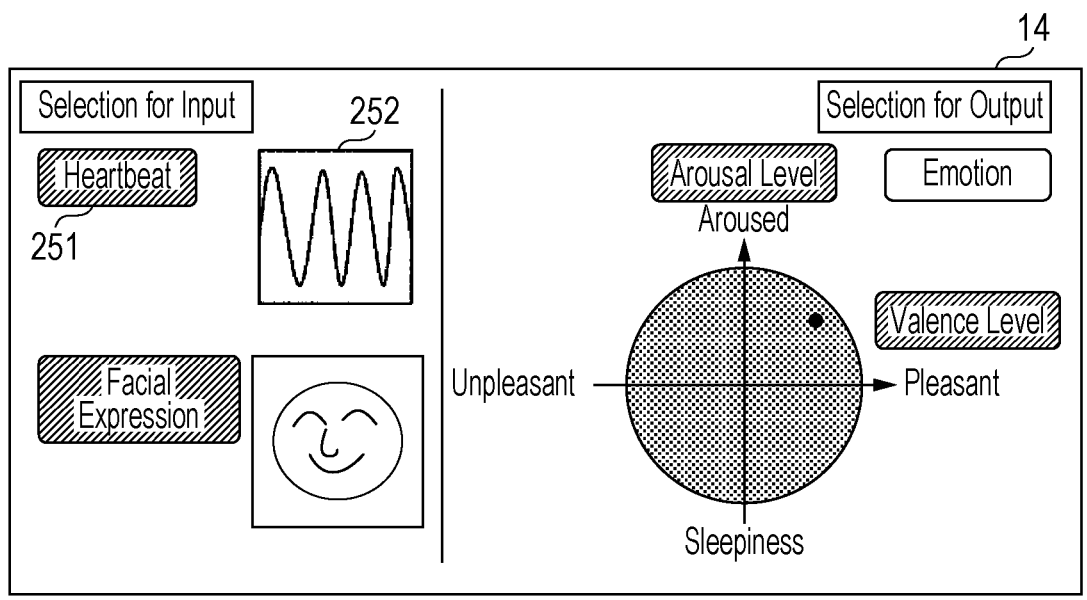
FIG. 25 is a schematic view of a sixth example of the image including the information indicating the emotion estimated by the estimator according to the embodiment.

FIG. 25 is a schematic view of a sixth example of the image including the information representing the emotion estimated by the estimator 30 according to the embodiment. The overall configuration of the image illustrated in FIG. 25 is substantially the same as the image illustrated in FIG. 22, and differs from that of the image illustrated in FIG. 22 in information indicating physiology data acquired from the subject U.

The left side in the image illustrated in FIG. 25 includes a button 251 for setting whether or not "heartbeat", which is physiology data, is to be acquired from the subject U and an image 252 showing time-series data of the waveform of acquired heartbeats.

Thus, the user or the subject U can recognize the emotion of the subject U which is estimated based on the heartbeats and the facial expression.

Figure 26A:
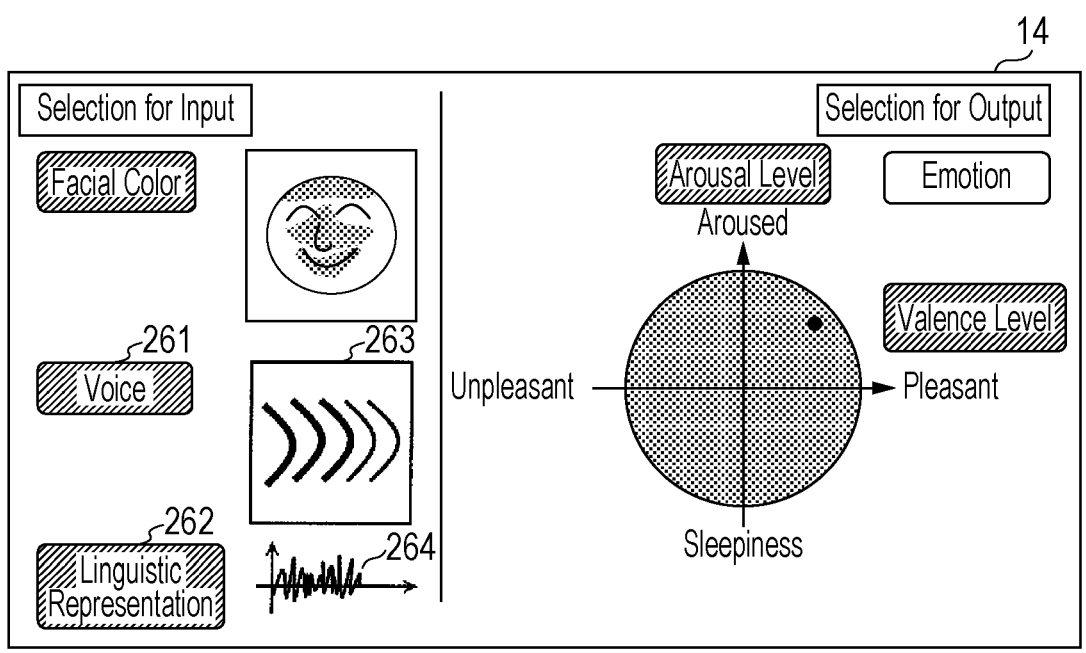
FIG. 26A is a schematic view of a seventh example of the image including the information indicating the emotion estimated by the estimator according to the embodiment.

FIG. 26A is a schematic view of a seventh example of the image including the information representing the emotion estimated by the estimator 30 according to the embodiment. The overall configuration of the image illustrated in FIG. 26A is substantially the same as the image illustrated in FIG. 22, and differs from that of the image illustrated in FIG. 22 in information indicating non-physiology data acquired from the subject U.

The left side in the image illustrated in FIG. 26A includes buttons 261 and 262 for setting whether or not voice and a linguistic representation, which are non-physiology data, are to be obtained from the subject U, an image 263 showing the intensity of obtained voice, and an image 264 showing the intensity of obtained linguistic expression.

Figure 26B:
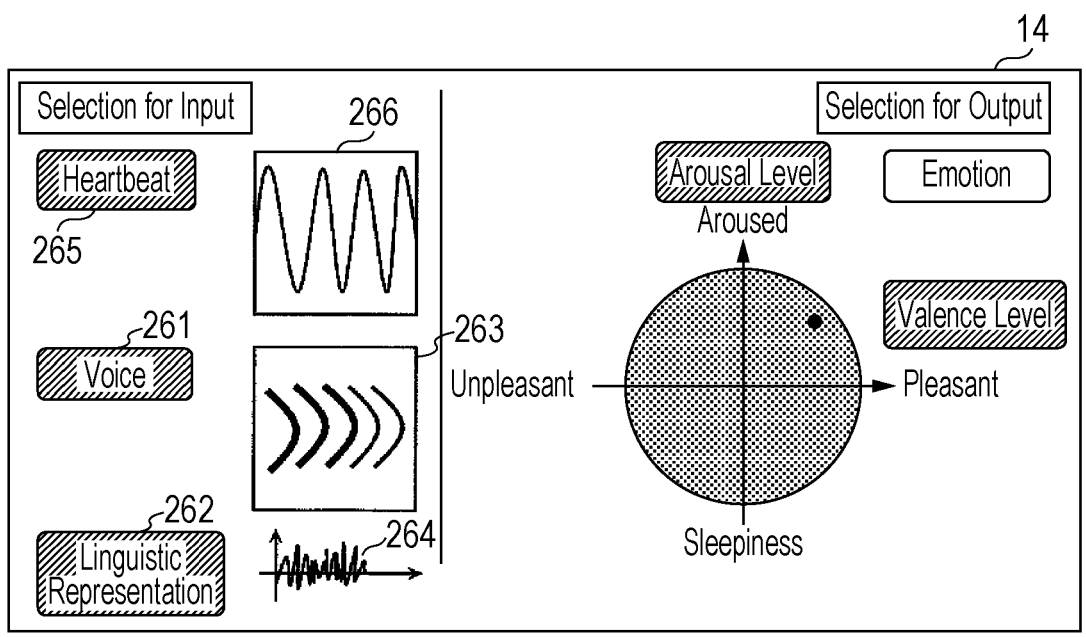
FIG. 26B is a schematic view of an eighth example of the image including the information indicating the emotion estimated by the estimator according to the embodiment.

FIG. 26B is a schematic view of an eighth example of the image including the information representing the emotion estimated by the estimator 30 according to the embodiment. The overall configuration of the image illustrated in FIG. 26B is substantially the same as the image illustrated in FIG. 26A, and differs from that of the image illustrated in FIG. 26A in information indicating physiology data acquired from the subject U.

The left side in the image illustrated in FIG. 26B includes a button 265 for setting whether or not "heartbeat", which is physiology data, is to be acquired from the subject and an image 266 showing the waveform of acquired heartbeats.

Thus, the user or the subject U can recognize the emotion of the subject U which is estimated based on the facial color, voice, and a linguistic representation.

FIG. 27 is a schematic view of an image for registering subject information according to the embodiment.

The image illustrated in FIG. 27 is displayed on the display device 14 in order to register, with the emotion estimating apparatus 10, information regarding the subject U whose emotion is to be estimated by the emotion estimating apparatus 10 (this information is also referred to as "subject information").

This image includes an image for receiving, from the user, operations for registering information regarding the subject U. Examples of the information include the nationality, the gender, the age, an average heart rate during a normal state, a blood pressure during a normal state, the skin color, and a chronic disease of the subject U. When the user performs an operation on any of areas in which the aforementioned pieces of information are displayed, the operation input IF 15 receives the operation, and control is performed so as to change data corresponding to the operated button. A known method, such as a method in which a user selects displayed options, such as settable characters or symbols, can be used for changing the data.

FIG. 28 is a schematic view of a first example of an image for registering the face of the subject U according to the embodiment.

The image illustrated in FIG. 28 is displayed on the display device 14 in order to register the face of the subject U whose emotion is to be estimated by the emotion estimating apparatus 10.

This image includes an image 281 showing the face of the subject U to be registered with the emotion estimating apparatus 10, a display area 282 indicating an average heart rate during a normal state, a display area 283 indicating an average respiration rate during a normal state, and a button 284 for the registration. The image 281 may be an image resulting from reading of data stored in a storage medium or may be an image resulting from photography with a camera when the emotion estimating apparatus 10 has the camera. The average heart rate and the average respiration rate may be input by the user or may be acquired by the sensor 13 from the user.

When the user performs an operation corresponding to the button 284, the operation input IF 15 receives the operation, and the image 281 when the operation was performed is registered as the face of the subject U. Based on the face of the subject U which is registered as described above, a facial expression, which is non-physiology data, is analyzed.

Figure 29:
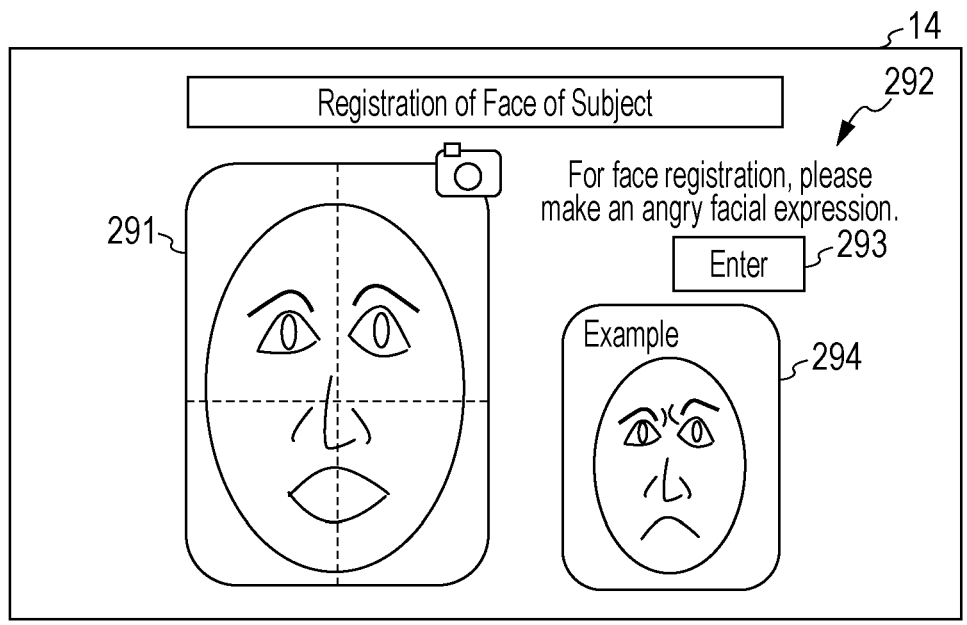
FIG. 29 is a schematic view of a second example of an image for registering the face of the subject according to the embodiment.

FIG. 29 is a block diagram of a second example of the image for registering the face of the subject U according to the embodiment.

The image illustrated in FIG. 29 is displayed on the display device 14 in order to register the face with various facial expressions of the subject U whose emotion is to be estimated by the emotion estimating apparatus 10.

This image includes an image 291 showing the face of the subject U to be registered with the emotion estimating apparatus 10, a button 293 for registration, and an image 294 for prompting the subject U to make a facial expression. When the emotion estimating apparatus 10 has a camera, a message 292 for prompting the subject U to make various facial expressions.

The image 291 may be an image resulting from reading of data stored in a storage medium or an image resulting photography with a camera when the emotion estimating apparatus 10 has the camera.

The message 292 is a message for prompting the subject U to make a facial expression (e.g., an angry facial expression) of the subject U to be registered. The subject U views the message 292 and makes a facial expression in accordance with the contents of the message 292.

When the user performs an operation on the button 293, the operation input IF 15 receives the operation, and the image 291 when the operation was performed is registered as the face of the subject U with the facial expression to be registered. Based on the face of the subject U which is registered as described above, a facial expression, which is non-physiology data, is analyzed. Although the number of the facial expressions to be registered may be two or more, for example, it is not necessary to register facial expressions corresponding to all emotions included in Russell's circumplex model (FIG. 1). This is because, for example, a method using movement of feature points or the like has already been known for an association between a human emotion and a facial expression, and a face with a predetermined emotion can be formed by moving the positions of feature points included in the registered face of the subject U on the basis of a predetermined relationship.

The image 294 is an image for prompting the subject U to make his or her facial expression. For example, when it is desired to make the subject U make an angry facial expression, the image 294 shows, as an example of the facial expression, an angry facial expression of the subject U which is generated by computer graphics on the basis of an image of the face of the subject U. The image 294 may be an image for making the subject U to feel an emotion so as to spontaneously make a facial expression. For example, when it is desired to register a smile of the subject U, the image 294 may be an image showing a smile of a person different from the subject U or may be an image of animal or the like. The image may also include words or a character representation (e.g., words "It's very beautiful, isn't it?").

Figure 30:
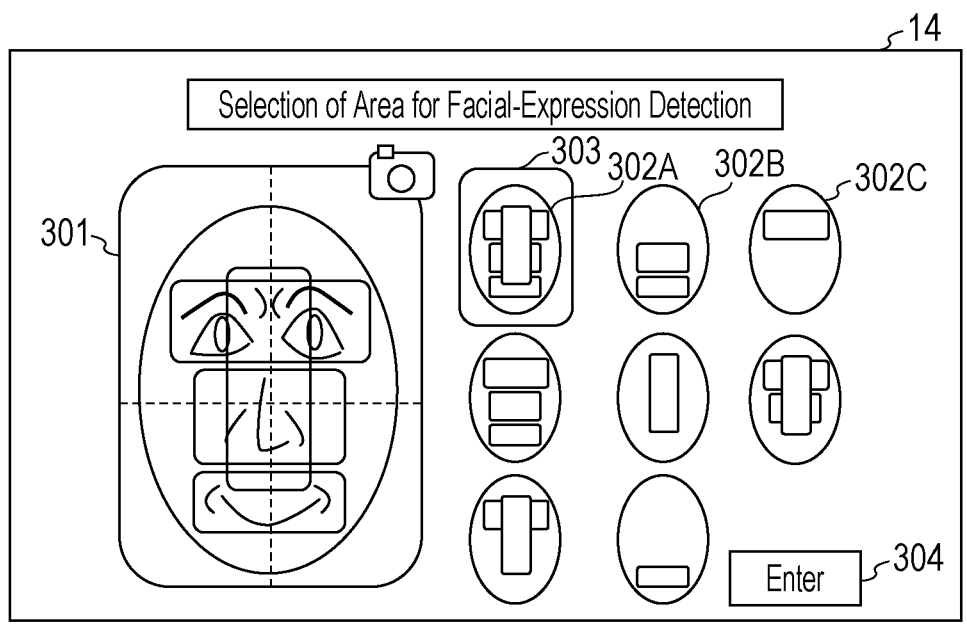
FIG. 30 is a schematic view of a first example of an image for selecting an area for detecting a facial expression from the face of the subject according to the embodiment.

FIG. 30 is a schematic view of a first example of an image for selecting an area for detecting a facial expression from the face of the subject U according to the embodiment. The image illustrated in FIG. 30 is displayed on the display device 14 in order to set a face area of the subject U from which a facial expression, which is non-physiology data, is to be acquired by the acquirer 20.

This image includes an image 301 in which a pattern of an area from which a facial expression is to be obtained is shown superimposed on the face of the subject U, images 302A, images 302B, and images 302C showing candidates of the pattern of the area, a cursor 303, and a button 304 for registration.

The image 301 is an image in which the pattern of the area included in the images 302A and specified by the cursor 303 is superimposed on the face of the subject U. The candidates of the pattern of the area are obtained as various patterns of combinations of characteristic portions obtained by segmenting the face. For example, the face is divided into a portion including the eyes on the face, a portion including the nose and the cheek, a portion including the nose and a region between the eyebrows, and a portion including the mouth, and these portions are combined into various combinations to thereby form the patterns of the areas, as illustrated in the images 302A and so on.

The cursor 303 specifies one of the images 302A and can be moved by a user operation.

When a user performs an operation on the button 304, the operation input IF 15 receives the operation, and the image 301 when the operation was performed is registered as the pattern of the area from which the facial expression is to be obtained.

Figure 31:
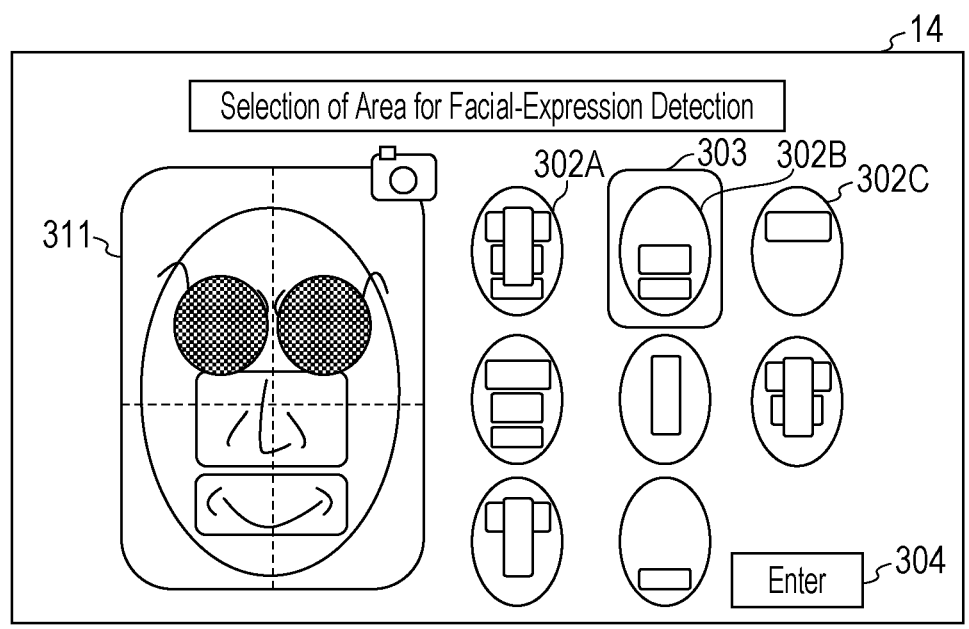
FIG. 31 is a schematic view of a second example of an image for selecting an area for detecting a facial expression from the face of the subject according to the embodiment.

FIG. 31 is a schematic diagram of a second example of the image for selecting an area for detecting a facial expression from the face of the subject U according to the embodiment. The overall configuration and rolls of the image illustrated in FIG. 31 are substantially the same as those of the image illustrated in FIG. 30.

A portion including the eyes on the face of the subject U included in the image 311 illustrated in FIG. 31 is covered with sunglasses, and it is thought to be difficult to analyze a facial expression on the basis of the eye portion. In such a case, the pattern of the area corresponding to the image 302B, which is the pattern of an area not including the eye portion, may be registered as the pattern of the area from which a facial expression is to be obtained.

When information regarding wrinkles of the face is included, it is possible to enhance the accuracy of a facial-expression or emotion determination made by the emotion estimating apparatus 10. In addition, when the emotion estimating apparatus 10 has a function for identifying an individual, it is also possible to enhance the accuracy of identifying an individual.

FIG. 32 illustrates an example of a screen for prompting the user to select whether or not information regarding wrinkles of the face is to be used when the emotion estimating apparatus 10 makes a facial-expression or emotion determination. In the example in FIG. 32, a message indicating that use of the information regarding wrinkles of the face can enhance the accuracy of the facial-expression and emotion determination may be presented to the user.

Modifications of Embodiments

In a modification, a description will be given of another configuration of the emotion estimating apparatus for estimating various emotions felt by a person. Constituent elements that are the same as or similar to those in the embodiment are denoted by the same reference numerals, and detailed descriptions are not given hereinafter.

Figure 33:
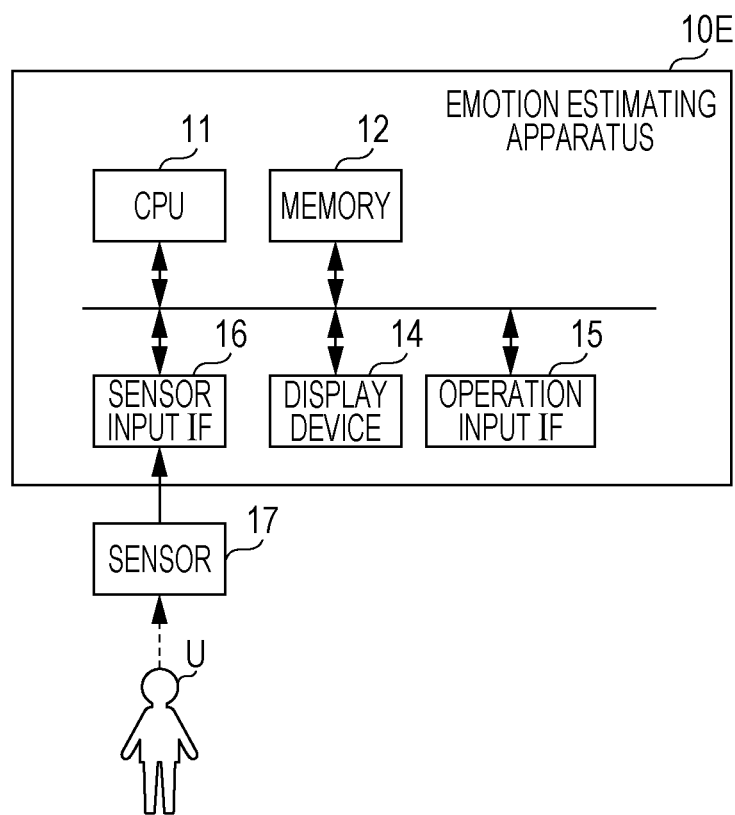
FIG. 33 is a block diagram illustrating the hardware configuration of an emotion estimating apparatus according to a modification of the embodiment.

FIG. 33 is a block diagram illustrating the hardware configuration of an emotion estimating apparatus 10E according to this modification.

As illustrated in FIG. 33, the emotion estimating apparatus 10E includes a CPU 11, a memory 12, a display device 14, an operation input IF 15, a sensor input IF 16, and a sensor 17. The emotion estimating apparatus 10E differs from the emotion estimating apparatus 10 in that the emotion estimating apparatus 10E has the sensor input IF 16 instead of the sensor 13.

The sensor input IF 16 is connected to the sensor 17 for acquiring, from the human subject U, physiology data or non-physiology data of the subject U. The sensor 17 may be the same as or similar to the sensor 13 in the emotion estimating apparatus 10.

In the emotion estimating apparatus 10E, the acquirer 20 acquires information from the sensor 17 via the sensor input IF 16 and performs processing that is analogous to that in the emotion estimating apparatus 10 in the embodiment.

With this configuration, the emotion estimating apparatus 10E can obtain information from the sensor 17 external to the emotion estimating apparatus 10E without provision of a sensor in the emotion estimating apparatus 10E and can estimate the emotion of a subject.

As described above, the emotion estimating apparatus in the embodiment can estimate an emotion of a subject on the basis of a predetermined association and through use of two or more pieces of data including physiology data acquired from the subject and physiology data different from that physiology data or non-physiology data acquired from the subject. Through use of the two or more pieces of data, the emotion estimating apparatus disclosed herein calculates two indicators, that is, a first value (an arousal level) and a second value (a valence level) of a subject, thereby making it possible to appropriately estimate various emotions felt by the subject.

Also, through use of the physiology data and non-physiology data acquired from the subject and based on basis of the predetermined association, the emotion estimating apparatus can estimate an emotion of the subject. The physiology data has a relatively high correlation with the arousal level, and the non-physiology data has a relatively high correlation with the valence level. Hence, when the physiology data and the non-physiology data are used, the arousal level and the valence level can be more accurately calculated, and thus, the emotion of the subject can be estimated with higher accuracy.

Also, the emotion estimating apparatus calculates an arousal level having a relatively high correlation with the physiology data through use of the physiology data acquired from the subject, and calculates a valence level having a relatively high correlation with the non-physiology data through use of the non-physiology data. Hence, the arousal level and the valence level can be more accurately calculated, and thus, the emotion of the subject can be estimated with higher accuracy.

Also, the emotion estimating apparatus acquires both the heart rate, which is physiology data, of the subject and a facial expression, which is non-physiology data, by using a camera and estimates the emotion of the subject. Thus, when both the physiology data and the non-physiology data are acquired using one device, which is a camera, to estimate the emotion, the amount of burden on the subject is reduced, and convenience improves.

The emotion estimating apparatus also outputs the arousal level and the valence level of the subject by representing the arousal level and the valence level as a point in a plane. This allows the user or the subject to intuitively know which of various possible subject emotions the emotion of the subject corresponds and also the intensity of the emotion of the subject.

The emotion estimating apparatus outputs at least one of the arousal level and the valence level of the subject. As a result of the outputting, the user or the subject can know not only the emotion of the subject but also the arousal level and/or the valence level felt by the subject.

Also, the emotion estimating apparatus outputs the intensity of a particular emotion (e.g., happiness) of the subject (in other words, the degree of an emotion). For example, the emotion estimating apparatus outputs not only an emotion "happiness" but also the degree of happiness. This allows the user or the subject to know not only the emotion of the subject but also the intensity or degree of the emotion.

Also, the emotion estimating apparatus outputs, as reliabilities, the level of correctness at which the estimated emotion represents the emotion of the subject. This allows the user or the subject to know not only the emotion of the subject but also the level of correctness at which the emotion represents the emotion of the subject.

Also, when the arousal level or the valence level can be obtained from a plurality of pieces of physiology data and non-physiology data, the emotion estimating apparatus can estimate an emotion of the subject by appropriately evaluating the plurality of pieces of physiology data and non-physiology data on the basis of the reliabilities.

In addition, the emotion estimating apparatus outputs a warning when the estimated emotion does not so correctly represent the emotion of the subject. This allows the user or the subject to clearly know that the estimated emotion does not so correctly represent the emotion of the subject.

Additionally, by varying the reference values for the arousal level and the valence level on the basis of information (e.g., the gender or age) relevant to a physical characteristic of the subject, the emotion estimating apparatus can adjust the arousal level and the valence level in accordance with the physical characteristic of the subject and can more appropriately estimate the emotion.

Also, upon receiving a setting for the face area for acquiring a facial expression of the subject, the emotion estimating apparatus acquires a facial expression of the subject by using the received setting. For example, when the subject wears sunglasses, the portion of the eyes of the subject is hidden by the sunglasses, and thus information regarding a facial expression cannot be obtained from the eye portion. In such a case, the emotion estimating apparatus is adapted to obtain a facial expression of the subject from a portion other than the eye portion of the subject to thereby make it possible to more appropriately detect the facial expression.

Also, by using the physiology data, such as facial color, the emotion estimating apparatus can more specifically estimate an emotion felt by the subject.

In addition, by using the non-physiology data, such as a facial expression, the emotion estimating apparatus can more specifically estimate an emotion felt by the subject.

Additionally, by using the information, such as gender, the emotion estimating apparatus can more specifically estimate an emotion felt by the subject.

In each embodiment described above, the individual constituent elements may be implemented by dedicated hardware or may be realized by executing a software program suitable for each constituent element. A program executor, such as a CPU or a processor, may read and execute a software program recorded in a storage medium, such as a hard disk or a semiconductor memory, to thereby realize the constituent elements. Herein, software for realizing the emotion estimating apparatus in each embodiment described above is, for example, a program as described below.

That is, this program causes a computer to execute an emotion estimating method for an emotion estimating apparatus for estimating an emotion of a subject. The emotion estimating method includes: acquiring first data and second data from a subject, the first data corresponding to physiology data, and the second data corresponding to one of physiology data and non-physiology data and being different from the first data; calculating a first value and a second value based on the acquired first data and second data, the first value indicating a degree of arousal of the subject and the second value indicating a degree of valence of the subject; estimating the emotion of the subject, by using the calculated first value and second value and based on a predetermined association of people's emotions with a degree of arousal and a degree of valence of the people, the predetermined association being pre-stored in a memory; and outputting information indicating the estimated emotion.

Although the emotion estimating apparatus and so on according to one or more aspects have been described above based on the embodiment, the present disclosure is not limited to the embodiment. Modes obtained by applying various modifications conceived by those skilled in the art to the embodiment or modes constituted by combining the constituent elements in different embodiments may also be encompassed by the scope of one or more aspects, as long as such modes do not depart from the spirit and scope of the present disclosure.

The present disclosure can be applied to an emotion estimating method, an emotion estimating apparatus, and so on that estimate various emotions felt by people.

What is claimed is:

1. An emotion estimating method for an emotion estimating apparatus for estimating an emotion of a subject, the emotion estimating method comprising:

acquiring, using a processor of the emotion estimating apparatus, first data and second data from the subject, the first data corresponding to physiology data, and the second data corresponding to one of physiology data different from the first data and non-physiology data;

calculating, using the processor, a first value indicating a degree of arousal of the subject based on a difference between a predetermined first reference value and a value indicated by the acquired first data, wherein the predetermined first reference value indicates a value indicated by physiology data corresponding to an arousal of which degree is 0;

calculating, using the processor, a second value indicating a degree of valence of the subject based on a comparison result obtained by comparing a value of the acquired second data with a predetermined second reference value;

estimating, using the processor, the emotion of the subject, by using the calculated first value and second value and based on a predetermined association of people's emotions with a degree of arousal and a degree of valence of the people, the predetermined association being pre-stored in a memory; and controlling, using the processor, a display of the emotion estimating apparatus to output an image indicating the estimated emotion on a display screen of the display, wherein the emotion estimating method further comprises:

controlling, using the processor, the display to output plural images on the display screen, each of the plural images indicating a candidate area which indicates one of a plurality of predetermined areas of a human face, each of the plurality of predetermined areas being used for acquiring a facial expression that is the second data, and the candidate area indicated by each of the plural images being different from other candidate areas; and controlling, using the processor, an input interface of the emotion estimating apparatus, to receive an instruction to select one of the plural images, wherein, in the acquiring, a feature point included in an area of a face of the subject corresponding to the one of the plurality of predetermined areas of the human face indicated by the selected one of the plural images is acquired as the second data, wherein the predetermined second reference value indicates a predetermined reference position of the feature point included in the one of the plurality of predetermined areas of the human face indicated by the selected one of the plural images, and wherein, in the calculating of the second value, the second value is calculated by comparing a position of the feature point included in the area of the face of the subject and the predetermined reference position indicated by the predetermined second reference value.

2. The emotion estimating method according to claim 1, wherein the second data is non-physiology data.

3. The emotion estimating method according to claim 2, wherein the emotion estimating apparatus comprises a camera that captures an image of the face of the subject to generate moving-image data, wherein, in the acquiring, a heart rate of the subject is acquired as the first data, based on the moving-image data generated by the camera, and a facial expression of the subject is acquired as the second data, the facial expression being identified based on a position of the feature point on the face of the subject in the moving-image data generated by the camera, wherein, the predetermined first reference value indicates a value of a heart rate of the human corresponding to the arousal of which degree is 0, and wherein, the predetermined second reference value indicates the predetermined reference position of the feature point.

4. The emotion estimating method according to claim 1, wherein, in the controlling, the display is further controlled to output an image indicating a point in a plane with two coordinate axes indicating the first value and the second value on the display screen as the image indicating the estimated emotion of the subject.

5. The emotion estimating method according to claim 1, wherein, in the controlling, the display is further controlled to output an image indicating at least one of the first value and the second value on the display screen as the image indicating the estimated emotion of the subject.

6. The emotion estimating method according to claim 1, wherein, in the calculating, a first reliability that is an indicator indicating correctness of the emotion of the subject, which is estimated based on the first value, is calculated, and a second reliability that is an indicator indicating correctness of the emotion of the subject, which is estimated based on the second value, is calculated; and wherein, in the controlling,
the display is further controlled to output an image indicating at least one of the first reliability and the second reliability on the display screen together with the image indicating the estimated emotion.

7. The emotion estimating method according to claim 6, wherein the first data acquired in the acquiring comprises one or more pieces of first data, and the second data acquired in the acquiring comprises one or more pieces of second data; and wherein, in the calculating,
a first value and a first reliability are calculated for each of the acquired one or more pieces of first data,
the first value is a value resulting from weighted average using the first reliability for the first value as a weight,
a second value and a second reliability are calculated for each of the acquired one or more pieces of second data, and
the second value is a value resulting from weighted average using the second reliability for the second value as a weight.

8. The emotion estimating method according to claim 6, wherein, in the controlling,
when at least one of the first reliability and the second reliability is smaller than a predetermined threshold, the display is further controlled to output an image indicating a warning on the display screen.

9. The emotion estimating method according to claim 1, wherein the emotion estimating method further comprises:
obtaining, using the input interface of the emotion estimating apparatus, information relevant to a physical characteristic of the subject; and
(i) adjusting, using the processor, the predetermined first reference value, based on the obtained information relevant to the physical characteristic of the subject,
wherein, in the calculating of the first value,
a difference between the first data and the adjusted predetermined first reference value is calculated, or
(ii) adjusting, using the processor, the predetermined second reference value, based on the obtained information relevant to the physical characteristic of the subject,
wherein, in the calculating of the second value,
the second data and the adjusted predetermined second reference value are compared.

10. The emotion estimating method according to claim 9, wherein the predetermined first reference value or the predetermined second reference value is calculated based on at least one of a gender, nationality, age, and skin color of the subject.

11. The emotion estimating method according to claim 1, wherein the physiology data includes at least one of face color, a heart rate, a heart rate variation, a low frequency/high frequency (LF/HF) of a heart rate variation, an R wave to R wave (R-R) interval, a pulse wave, a pulse variation, a brain wave, a respiration rate, a respiratory volume, a blood flow, a blood flow variation, a blood pressure, a blood pressure variation, an oxygen saturation level, movement of a part of a human body, movement of a muscle of a human body, movement of a muscle of a face, a body temperature, a skin temperature, a skin conductance, a skin resistance, an amount of sweat, and a perspiration rate.

12. The emotion estimating method according to claim 1, wherein the non-physiology data includes at least one of a facial expression, an emotion, a touch input signal, voice, a linguistic representation, a sentence, and body motion.

13. The emotion estimating method according to claim 1, wherein, in the controlling, the display is further controlled to output, on the display screen, at least one of (i) a facial color of the subject associated with the first data and (ii) a facial expression of the subject associated with the second data.

14. The emotion estimating method according to claim 1, wherein, the method further comprises:
calculating, using the processor, a first reliability that is an indicator indicating correctness of the emotion of the subject, which is estimated based on the first value;
calculating, using the processor, a second reliability that is an indicator indicating correctness of the emotion of the subject, which is estimated based on the second value;
controlling, using the processor, the display to output, on the display screen of the display, (i) an image indicating the calculated first reliability, (ii) an image indicating the calculated second reliability, (iii) a first button to adjust the calculated first reliability and (iv) a second button to adjust the calculated second reliability; and
adjusting, using the processor, (i) the first value using the first reliability adjusted by the first button or (ii) the second value using the second reliability adjusted by the second button,
wherein, the emotion of the subject is estimated by using (i) one of the first value and the second value which is adjusted by the adjusting, (ii) another of the first value and the second value and (iii) the predetermined association, or
wherein, the emotion of the subject is estimated by using (i) the first value and the second value both of which are adjusted by the adjusting and (ii) the predetermined association.

15. An emotion estimating apparatus comprising:
a display; and
a processor that:
acquires first data and second data from a subject, the first data corresponding to physiology data, and the second data corresponding to one of physiology data and non-physiology data and being different from the first data;
calculates a first value indicating a degree of arousal of the subject based on a difference between a predetermined first reference value and a value indicated by the acquired first data, wherein the predetermined first reference value indicates a value indicated by the physiology data corresponding to an arousal of which degree is 0;
calculates, using the processor, a second value indicating a degree of valence of the subject based on a comparison result obtained by comparing the acquired second data with a predetermined second reference;
estimates the emotion of the subject, by using the calculated first value and second value and based on a predetermined association of people's emotions with a degree of arousal and a degree of valence of the people, the predetermined association being pre-stored in a memory; and controls the display to output an image information indicating the estimated emotion on a display screen of the display, wherein the processor further controls the display to output plural images on the display screen, each of the plural images indicating a candidate area which indicates one of a plurality of predetermined areas of a human face, each of the plurality of predetermined areas being used for acquiring a facial expression that is the second data, and the candidate area indicated by each of the plural images being different from other candidate areas; and wherein the emotion estimating apparatus further includes an input interface that receives an instruction to select one of the plural images, wherein, in the acquiring, a feature point included in an area of a face of the subject corresponding to the one of the plurality of predetermined areas of the human face indicated by the selected one of the plural images is acquired as the second data, wherein the predetermined second reference value indicates a predetermined reference position of the feature point included in the one of the plurality of predetermined areas of the human face indicated by the selected one of the plural images, and wherein, in the calculating of the second value, the second value is calculated by comparing a position of the feature point included in the area of the face of the subject and the predetermined reference position indicated by the predetermined second reference value.

16. A non-transitory recording medium storing a computer program, the program causing a computer to execute:

acquiring first data and second data from a subject, the first data corresponding to physiology data, and the second data corresponding to one of physiology data and non-physiology data and being different from the first data;

calculating a first value indicating a degree of arousal of the subject based on a difference between a predetermined first reference value and a value indicated by the acquired first data, wherein the predetermined first reference value indicates a value indicated by the physiology data corresponding to an arousal of which degree is 0;

calculating, using the processor, a second value indicating a degree of valence of the subject based on a comparison result obtained by comparing the acquired second data with a predetermined second reference;

estimating the emotion of the subject, by using the calculated first value and second value and based on a predetermined association of people's emotions with a degree of arousal and a degree of valence of the people, the predetermined association being pre-stored in a memory; and controlling a display of the computer to output an image information indicating the estimated emotion on a display screen of the display, wherein the program further causes the computer to execute:

controlling the display of the computer to output plural images on the display screen, each of the plural images indicating a candidate area which indicates one of a plurality of predetermined areas of a human face, each of the plurality of predetermined areas being used for acquiring a facial expression that is the second data, and the candidate area indicated by each of the plural images being different from other candidate areas; and controlling an input interface of the computer to receive an instruction to select one of the plural images, wherein, in the acquiring, a feature point included in an area of a face of the subject corresponding to the one of the plurality of predetermined areas of the human face indicated by the selected one of the plural images is acquired as the second data, wherein the predetermined second reference value indicates a predetermined reference position of the feature point included in the one of the plurality of predetermined areas of the human face indicated by the selected one of the plural images, and wherein, in the calculating of the second value, the second value is calculated by comparing a position of the feature point included in the area of the face of the subject and the predetermined reference position indicated by the predetermined second reference value.

* * * * *